(12) United States Patent
Charles et al.

(10) Patent No.: US 12,318,513 B2
(45) Date of Patent: Jun. 3, 2025

(54) DISINFECTION DEVICES AND METHODS USING THE SAME

(71) Applicant: SoClean, Inc., Peterborough, NH (US)

(72) Inventors: Robert A. Charles, New Boston, NH (US); Kurt Michael Maw, Salem, MA (US); Pete McNulty, Peterborough, NH (US); Katja Lierhaus, Peterborough, NH (US)

(73) Assignee: SOCLEAN, INC., Peterborough, NH (US)

( * ) Notice: Subject to any disclaimer, the term of this patent is extended or adjusted under 35 U.S.C. 154(b) by 917 days.

(21) Appl. No.: 17/490,887

(22) Filed: Sep. 30, 2021

(65) Prior Publication Data

US 2022/0105221 A1 Apr. 7, 2022

Related U.S. Application Data

(60) Provisional application No. 63/087,047, filed on Oct. 2, 2020.

(51) Int. Cl.
*A61L 9/12* (2006.01)
(52) U.S. Cl.
CPC .......... *A61L 9/122* (2013.01); *A61L 2202/122* (2013.01); *A61L 2202/123* (2013.01); *A61L 2202/24* (2013.01); *A61L 2209/14* (2013.01)
(58) Field of Classification Search
CPC ............... A61L 9/122; A61L 2202/122; A61L 2202/123; A61L 2202/24; A61L 2209/14; A61L 2202/11; A61L 2202/13; A61L 2202/14; A61L 2/202
USPC ........................................................ 422/124
See application file for complete search history.

(56) References Cited

U.S. PATENT DOCUMENTS

| | | | |
|---|---|---|---|
| 8,865,065 B2* | 10/2014 | Kain | A61L 2/24 422/1 |
| 2003/0152480 A1* | 8/2003 | Sham | A61L 2/202 422/1 |

* cited by examiner

*Primary Examiner* — Huy Tram Nguyen
(74) *Attorney, Agent, or Firm* — Grossman, Tucker, Perreault & Pfleger, PLLC

(57) ABSTRACT

Disinfection devices and methods of using the same are described. In embodiments the disinfection devices include a base, a lid, a sanitizing gas supply, a sanitization chamber with an exhaust port and chamber opening, and a fan. When the lid is closed the fan can operate in a first (low flow, high static pressure) flow condition, during which gas may flow through the device at a first (relatively low) flow rate. When the lid is open the fan can operate in a second (high flow, low static pressure) flow condition, during which the fan may exhaust all or substantially all sanitizing gas in the sanitization chamber through the exhaust port over a short exhaust period. The systems and methods can enable a user to rapidly access an article being sanitized with little or no risk of exposure to the sanitizing gas, even when a disinfection operation is in process.

20 Claims, 12 Drawing Sheets

DISINFECTION DEVICES AND METHODS USING THE SAME

TECHNICAL FIELD

The present disclosure is generally directed to disinfection devices that can provide rapid access to an article being disinfected with a sanitizing gas. Disinfection methods using such devices are also described.

BACKGROUND INFORMATION

Over time the surfaces of various articles (e.g., consumer devices, medical devices, etc.) can become fouled with contaminants such as bacteria, viruses, and the like. Without proper sanitization (i.e. disinfection at an acceptable log performance) such articles can contribute to the spread of harmful bacteria and/or viruses, and may present a health risk to end users.

Various systems and methods have been developed to disinfect articles such as medical devices. While such systems are useful they are not without limitations. For example, some sanitizing systems use ultraviolet (UV) light to sanitize articles such as smart phones. If part of the article being sanitized is obscured from the UV light, however, that portion of the article will not be adequately sanitized. While optics such as minors can address that issue to some degree, they increase the complexity and cost of manufacturing a UV sanitizing system, and may still not ensure that the entire surface of an article being sanitized is exposed to UV light.

Systems that disinfect articles (e.g., medical devices) in a sanitization chamber with a sanitizing gas have also been developed. Because the sanitizing gas can flow around and/or through an article, such systems can effectively sanitize articles that have a complex shape and/or which have surfaces that are difficult to clean manually (e.g., tubing). To prevent a user from being exposed to the sanitizing gas, such systems may prevent access to the sanitization chamber during a disinfection operation (i.e., while article is being sanitized) and during a relatively long waiting period following the performance of a disinfection operation. Although imposed for safety reasons, users may find such features undesirable when they wish to access an article in the sanitization chamber during a disinfection operation or during the waiting period. This is particularly true when the article being sanitized is a smart phone or other device to which a user may wish to have immediate access.

Accordingly, there is a need in the art for improved disinfection devices, e.g., that can allow rapid access to an article that is being disinfected with a sanitizing gas.

BRIEF DESCRIPTION OF THE DRAWINGS

Features and advantages of embodiments of the claimed subject matter will become apparent as the following Detailed Description proceeds, and upon reference to the Drawings, wherein like numerals depict like parts, and in which:

DETAILED DESCRIPTION

Figure 1:
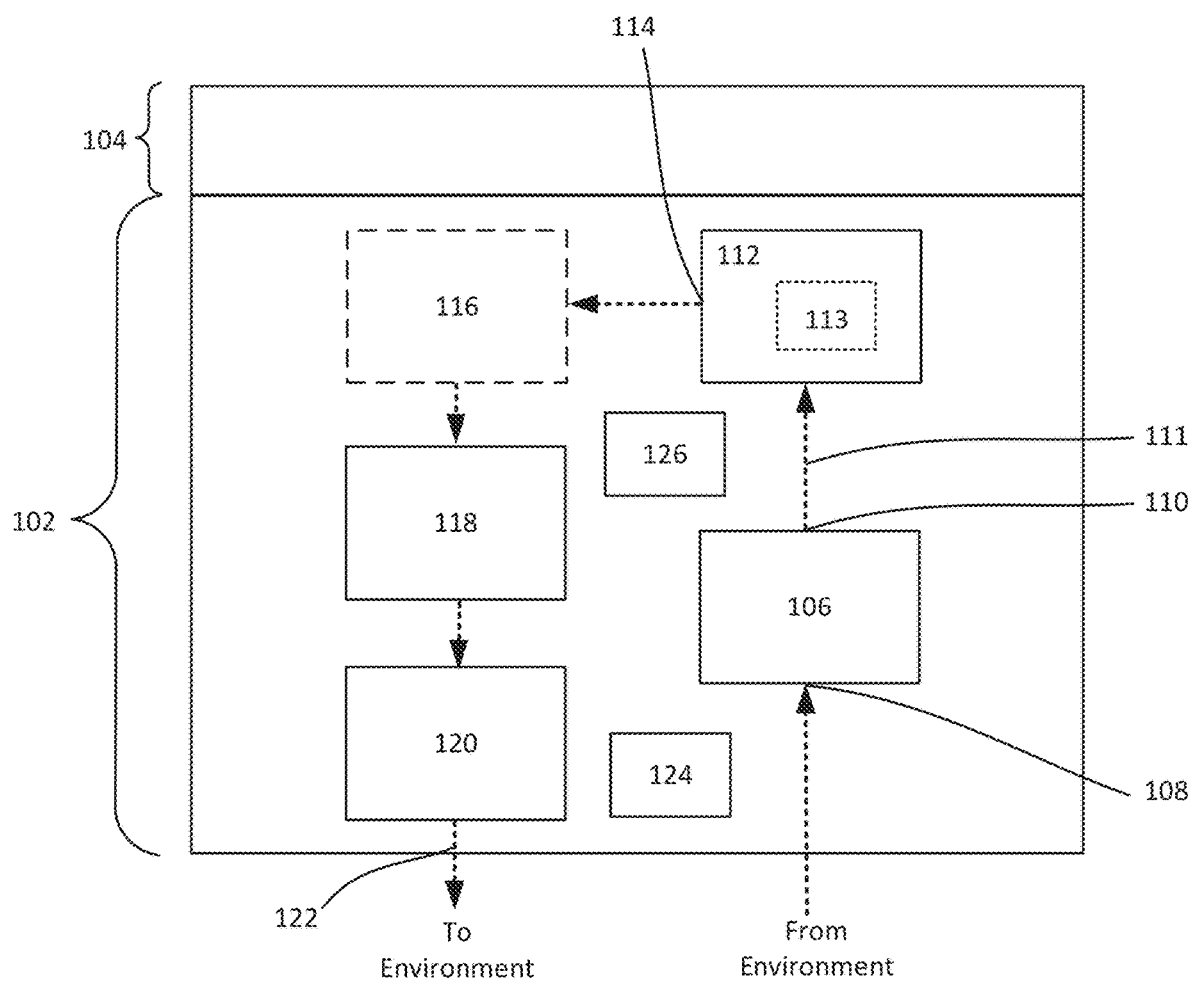
FIG. 1 is a block diagram of one example of a disinfection device with a fan downstream of a filter, consistent with the present disclosure.

As used herein the term "about," when used in connection with a value or a range, means plus or minus 5% of the indicated value or the endpoints of the range. Thus, for example, about 5% means 4.75% to 5.25%. Similarly, about 5 to about 10% means 4.75 to 10.5.

From time to time the present application describes features using numerical ranges. Such ranges should be understood to include the recited endpoints, and to encompass any intermediate ranges within the stated range. Thus, for example, the range "1 to 10" should be understood to include the endpoints 1 and 10, as well intermediate ranges therein (e.g., from 1 to 9, 2 to 10, 2 to 9, 3 to 9, 4 to 9, etc.) as if those intermediate ranges were expressly recited.

The present disclosure is generally directed to disinfection devices and methods of using the same. In embodiments the disinfection devices include a base and a lid that is movable between an open and a closed position. The devices further include a sanitizing gas supply, a sanitization chamber including or fluidly coupled to an exhaust port, and a fan. The devices may further include an exhaust channel downstream of the exhaust port, a filter, and a discharge outlet. The sanitizing gas supply (e.g. an ozone generator) is configured to generate a sanitizing gas (e.g., ozone). The fan is configured to operate in a first flow condition during a disinfection operation, and in a second flow condition during a termination operation. In embodiments the first flow condition is a low flow, high static pressure condition, and the second flow condition is a high flow, low static pressure condition. The fan is configured such that in the first flow condition gas flows through the fan at a first (relatively low) flow rate, and in the second flow condition gas flows through the fan at a second (relatively high) flow rate. In embodiments, the first and second flow rates can be achieved without adjusting the voltage applied to the fan.

During a disinfection operation the lid is closed, the sanitizing gas supply (e.g., an ozone operating system including an ozone generator) provides a sanitizing gas (e.g., ozone), and the fan operates in the first flow condition. Operation of the fan in the first flow condition causes the sanitizing gas to be drawn from the sanitizing gas supply into the sanitization chamber, where it can disinfect one or more articles therein. A controller may cause the fan to continuously or intermittently operate in the first flow condition, causing the sanitizing gas to continuously or intermittently flow into the sanitization chamber. At least a portion of the sanitizing gas may be removed from the sanitization chamber via the exhaust port to form an unfiltered exhaust stream downstream of the exhaust port. The unfiltered exhaust stream may be directed through the filter, either directly or via an optional exhaust channel. The filter may be configured to remove all or a portion of the sanitizing gas, e.g., by converting the sanitizing gas (e.g., ozone) into a breathable gas (e.g., oxygen). The resulting filtered exhaust stream may then be directed out of the device, e.g., via a discharge outlet.

In embodiments during a disinfection operation only a single (i.e., first) flow path is present through the disinfection device. The first flow path may extend from an inlet to the sanitizing gas supply, through the sanitizing gas supply, through the sanitization chamber, through the exhaust port, through the exhaust channel (if present), through a filter (if present), through the fan, and through the distribution outlet. While the first flow path is preferably configured in that manner, the first flow path may be configured in another manner. For example, the first flow path may include different/other elements, and the elements therein may be arranged in any suitable manner with a corresponding change in gas flow.

The first flow path includes a restricted portion. In embodiments the restricted portion of the first flow path extends at least partially through the sanitizing gas supply. The restricted portion of the first flow path (or, more particularly, the size of the passages through which gas flows in the restricted portion) may be sized such that it is relatively small compared to the size of the fan intake. For example, a passageway through inlet to the sanitizing gas supply (or another portion of the sanitizing gas supply) may have a first cross sectional area that is smaller than a second cross sectional area of the fan intake. Due to the flow restriction, the fan will operate in the first flow condition (i.e., a high pressure, low flow condition) when the lid is closed and gas may flow through the disinfection device at a first (relatively low) flow rate.

Operation of the fan in the first flow condition may cause a pressure differential to develop between the fan and the inlet to the sanitization gas supply. That pressure differential may cause gas (including sanitization gas) to flow from the sanitization gas supply into the sanitization chamber, either directly or via a distribution line and/or a diffuser within the sanitization chamber. The pressure differential in the first flow condition may also be sufficient to prevent sanitizing gas from leaking out of the inlet to the sanitizing gas supply. Thus, unlike some systems, the disinfection devices described herein do not require the use of a sanitizing gas supply that includes a fan for directing sanitizing gas into a sanitization chamber. Put differently, the disinfection devices described herein may be configured to operate with only a single fan downstream of the exhaust port. Moreover, while operation of the fan in the first flow condition may cause some sanitizing gas to be removed from the sanitization chamber during a disinfection operation, acceptable disinfection not an article within the sanitization chamber can still be achieved.

In embodiments the pressure differential in the first flow is a vacuum pressure ranging from greater than 0 to about 0.25 pounds per square inch (PSI), such as from greater than 0.005 to about 0.1 PSI, from greater than 0.01 to about 0.1 PSI, from greater than 0.01 to about 0.05 PSI, or even from greater than 0.01 to about 0.03 PSI. In embodiments, the vacuum pressure in the first flow condition ranges from about 0.018 to about 0.033 PSI.

During a termination operation the lid is moved to the open position, supply of the sanitizing gas (e.g., ozone) is stopped, and the fan is operated in the second flow condition. In the second flow condition the fan may be operated at a second voltage that is the same or higher than a first voltage applied to the fan during the first flow condition (i.e., during a disinfection operation). When the lid is in the open position a chamber opening providing access to the sanitization chamber is exposed to the atmosphere (e.g., air) and a second flow path through the device is provided. The second flow path may extend from the chamber opening, through at least part of the sanitization chamber, through the exhaust port, through the discharge channel (if present), through the filter (if present), through the fan, and through the discharge outlet. While that is a preferred configuration of the second flow path, it is not required and the elements noted above may be rearranged and/or removed with a corresponding change in flow path. Additional elements may also form part of the second flow path.

The size of the second flow path (or, more particularly, the cross sectional area of the passages through which gas flows in the second flow path) is relatively large compared to the size (i.e., cross sectional area) of the passageway(s) in the restricted portion of the first flow path. As a result, the second flow path is less restricted than the first flow path and enables the fan to operate in the second flow condition (i.e., a high flow, low pressure condition) during a termination operation.

As noted above, during a termination operation the fan operates in the second flow condition and gas flows from the sanitization chamber to the distribution outlet at a second (relatively high) flow rate. Because the lid is open during a termination operation, a copious amount of air is drawn into the chamber opening of the sanitization chamber and through the exhaust port. The incoming air flow entrains and dilutes sanitizing gas in the sanitization chamber, and causes the sanitizing gas to flow into the exhaust port, e.g., at the second flow rate. Because the second flow rate is relatively high, the sanitizing gas may be rapidly evacuated from the sanitization chamber.

For example the disinfection devices described herein may be configured such that during a termination operation, all or substantially all the sanitizing gas within the sanitization chamber may be removed from the sanitization chamber through the exhaust port within an exhaust period. In embodiments the exhaust period is less than or equal to about 20 seconds, less than or equal to about 10 seconds, such as less than or equal to about 5 seconds, less than or equal to about 3 seconds, less than or equal to about 1 second, less than or equal to about 0.5 seconds, or even less than or equal to about 0.1 seconds. In embodiments, the systems described herein are configured such that the exhaust period in the second flow condition exhausts all or substantially all of the sanitizing gas from the sanitization chamber in less than or equal to about 2 seconds, such as less than or equal to about 1 second, or even less than about 0.5 seconds.

As used herein, the term "substantially all of the sanitizing gas" when used in reference to the exhaust period means that the amount of sanitizing gas remaining in the sanitization chamber following the exhaust period (i.e., the residual amount of sanitizing gas) is less than a threshold amount. In embodiments, the residual amount of sanitizing is less than or equal to about 0.5 parts per million (ppm), such as less than or equal to about 0.05 ppm. In non-limiting embodiments, the residual amount of sanitizing gas remaining in the sanitization chamber following the exhaust period is 0. As may therefore be appreciated, a user can rapidly gain access to an article in the sanitization chamber simply by opening the lid of the disinfection device, with little or no risk of exposure to the sanitizing gas.

FIG. 1 is a block diagram of one example of a disinfection device consistent with the present disclosure. Disinfection device 100 includes a base 102 and a lid 104. The lid 104 is configured to move between an open position and a closed position. A sanitizing gas supply 106 is located within the base 102, and includes an inlet 108 and an outlet 110 fluidly coupled to a sanitization chamber 112, either directly or via a distribution line 111.

Sanitizing gas supply 106 may be any device or system that is configured to supply a sanitizing gas for use in sanitizing articles within sanitization chamber 112. In embodiments sanitizing gas supply 106 is or includes an ozone generator that is configured to generate ozone gas, e.g., from air. In such embodiments, the ozone generator may include inlet 108 and outlet 110, wherein the inlet 108 is fluidly coupled to a source of air and the outlet is fluidly coupled to sanitization chamber 112. In such embodiments and as discussed further below, the ozone generator may include one or more passageways that form at least part of a restricted portion of a first fluid pathway through disinfection device 100. Notably, in some embodiments the sanitizing gas supply 106 may lack a fan/pump that is configured to provide the sanitizing gas to sanitization chamber 112.

The sanitization chamber 112 is configured to receive at least one article 113 to be sanitized therein. Article 113 may be any article that can fit within sanitization chamber 112 while lid 104 is closed. Non limiting examples of articles that may be used as article 113 include keys, wallets, jewelry, eyeglasses, electronics (e.g., smart phones, tablets, laptops, etc.) combinations thereof, and the like. In embodiments the sanitization chamber 112 includes a chamber opening (not labeled) that is accessible when lid 104 is in the open position and which is closed off by at least a portion of lid 104 when lid 104 is in the closed position. A gas tight seal may be formed between the lid and a peripheral surface of the sanitization chamber 112, e.g., a rim around the chamber opening. As will be discussed further below, the disinfection devices described herein may include an upper and lower housing, and the sanitization chamber 112 may be in the form of an insert that is configured to be at least partially disposed within the lower housing, the upper housing, or both the lower and upper housings.

The sanitization chamber 112 includes or is fluidly coupled to an exhaust port 114. The exhaust port 114 may have any suitable shape, and in embodiments includes or is in the form of one or more openings that are formed through a wall (e.g., a side, a bottom, a top, combinations thereof, etc.) of the sanitization chamber 112. In specific non-limiting embodiments, the exhaust port 114 is in the form of one or a plurality (e.g., greater than or equal to 2, 3, 4, 5, 10, or more) openings through a wall (e.g., a side, a bottom, or a combination thereof) of the sanitization chamber 112. Such openings may have any suitable shape. In embodiments the exhaust port includes a plurality of geometric (e.g., circular, triangular, quadrilateral, oval, elliptical, etc.) openings, irregular shaped openings, or a combination thereof. Regardless of their shape, the exhaust port 114 is configured to receive gas from the sanitization chamber 112 and convey the gas as at least part of an unfiltered exhaust stream to one or more downstream components.

Disinfection device 100 further includes a filter 118 that is positioned downstream of the exhaust port 114. The filter 118 may be configured to receive the unfiltered exhaust stream in any suitable manner. For example, the filter 118 may be configured to fluidly couple to the exhaust port 114, either directly or through optional exhaust channel 116. In embodiments, optional exhaust channel 116 is omitted, the filter 118 includes a filter inlet and a filter outlet, and the filter inlet is configured to couple directly to the exhaust port 114. Alternatively, optional exhaust channel 116 is present and is configured to provide at least a portion of a flow path between exhaust port 114 and filter 118. For example, optional exhaust channel 116 may include a passage with a proximal end and a distal end, wherein the proximal end is configured to fluidly (or directly) couple to the exhaust port 114, and the distal end is configured to fluidly (or directly) couple to the filter inlet of filter 118. In such embodiments the inlet of the filter 118 may be configured to fluidly or directly couple to the distal end of the exhaust channel 116.

Filter 118 may be configured in any suitable manner, and may be integral with or removable from disinfection device 100. In embodiments filter 118 is in the form of a filter cartridge that is configured to be installed and removed from disinfection device 100. The filter cartridge may include a filter housing and a filter media in the filter housing. Consistent with the foregoing discussion, the filter housing may include a filter inlet and a filter outlet, and may be configured such that the filter inlet fluidly (or directly) couples with the exhaust port 114 and/or optional exhaust channel 116 when it is installed within disinfection device 100.

While the figures and description focus on embodiments in which a filter 118 is received within base 102, such a configuration is not required and the systems described herein may be configured such that filter 118 is in a different location. For example, the systems described herein may be configured such that filter 118 is located in lid 104, within one or more sidewalls of the sanitization chamber 112 and or a housing of the system, combinations thereof, and the like.

In any case filter 118 (or, more specifically, a filter media therein) is configured to reduce the amount of sanitizing gas within the unfiltered exhaust stream and to produce a filtered exhaust stream. More specifically, filter 118 may be configured to receive an unfiltered exhaust stream that contains a first amount of sanitizing gas and produce a filtered exhaust stream that contains a second amount of sanitizing gas, wherein the second amount of sanitizing gas is less than the first amount of sanitizing gas. In embodiments the first amount of sanitizing gas (e.g., ozone) may be greater than or equal to about 50 parts per million (ppm), e.g., greater than or equal to about 100 ppm, about 150 ppm, about 200 ppm, about 250 ppm, about 300 ppm, 350 ppm, about 400 ppm and even greater than or equal to 450 ppm. In those or other embodiments second amount of sanitizing gas may be less than 50 ppm, such as less than about 25 ppm, less than about 10 ppm, less than about 5 ppm, less than about 1 ppm, less than about 0.5 ppm, or even less than about 0.05 ppm. In specific non-limiting embodiments the second amount of sanitizing gas may be 0. Put differently, the filter 118 may reduce the amount of sanitizing gas in the unfiltered exhaust stream by at least about 50%, e.g., at least about 60%, at least about 70%, at least about 80%, at least about 90%, at least about 95%, at least about 99%, at least about 99.9%, or even 100%.

The filter 118 may reduce the amount of sanitizing gas in the unfiltered exhaust stream in any suitable manner, such as via absorption of the sanitizing gas, adsorption of the sanitizing gas, conversion of the sanitizing gas, or a combination thereof. In embodiments filter 118 is configured to convert sanitizing gas in the unfiltered exhaust stream to a breathable gas. For example when the sanitizing gas is ozone, filter 118 may include a conversion media that is configured to convert at least a portion of the ozone in the unfiltered exhaust stream to oxygen. Non-limiting examples of materials that may be used as such filter media include activated carbon, magnesium oxide, magnesium dioxide, manganese dioxide, zeolite, combinations thereof or the like, all of which can facilitate the conversion of ozone to oxygen.

Filter 118 is fluidly coupled to a fan 120 in any suitable manner. For example, the filter outlet of filter 118 may be directly coupled to the intake of fan 120. Alternatively, the filter outlet of filter 118 may be fluidly coupled to a proximal end of a first discharge conduit (e.g., a hose, a tube, a pipe, etc.), wherein the distal end of the first discharge conduit is fluidly coupled to the intake of fan 120.

Fan 120 (and the other fans described herein) may be any device that is capable of moving a fluid, such as a gas. Non-limiting examples of such devices include axial fans, centrifugal fans, turbines, pumps, compressors, blowers, combinations thereof, and the like. In embodiments, fan 120 is one or more axial or centrifugal fans. In specific embodiments, fan 120 is a single centrifugal fan.

In general, the fans described herein are configured to operate on a pressure/flow curve that is specific to the fan design. Depending on the resistance to gas flow within the disinfection device, the fans will generate a static pressure that causes gas to flow through the disinfection device at a defined flow rate. With that in mind, the disinfection devices described herein are configured to transition between a first flow condition in which the resistance to gas flow is high, and a second flow condition in which the resistance to gas flow is low.

Disinfection device 100 further includes a discharge outlet 122 that is configured to receive the filtered exhaust stream produced by filter 118 in any suitable manner. For example and as shown in FIG. 1, discharge outlet 122 may be fluidly coupled to fan 120. In operation, fan 120 may be configured to cause the filtered exhaust stream produced by filter 118 to flow through discharge outlet 122, e.g., by drawing the filtered exhaust stream into the fan intake (not shown), blowing it out the fan outlet (not shown) and through the discharge outlet.

Figure 2:
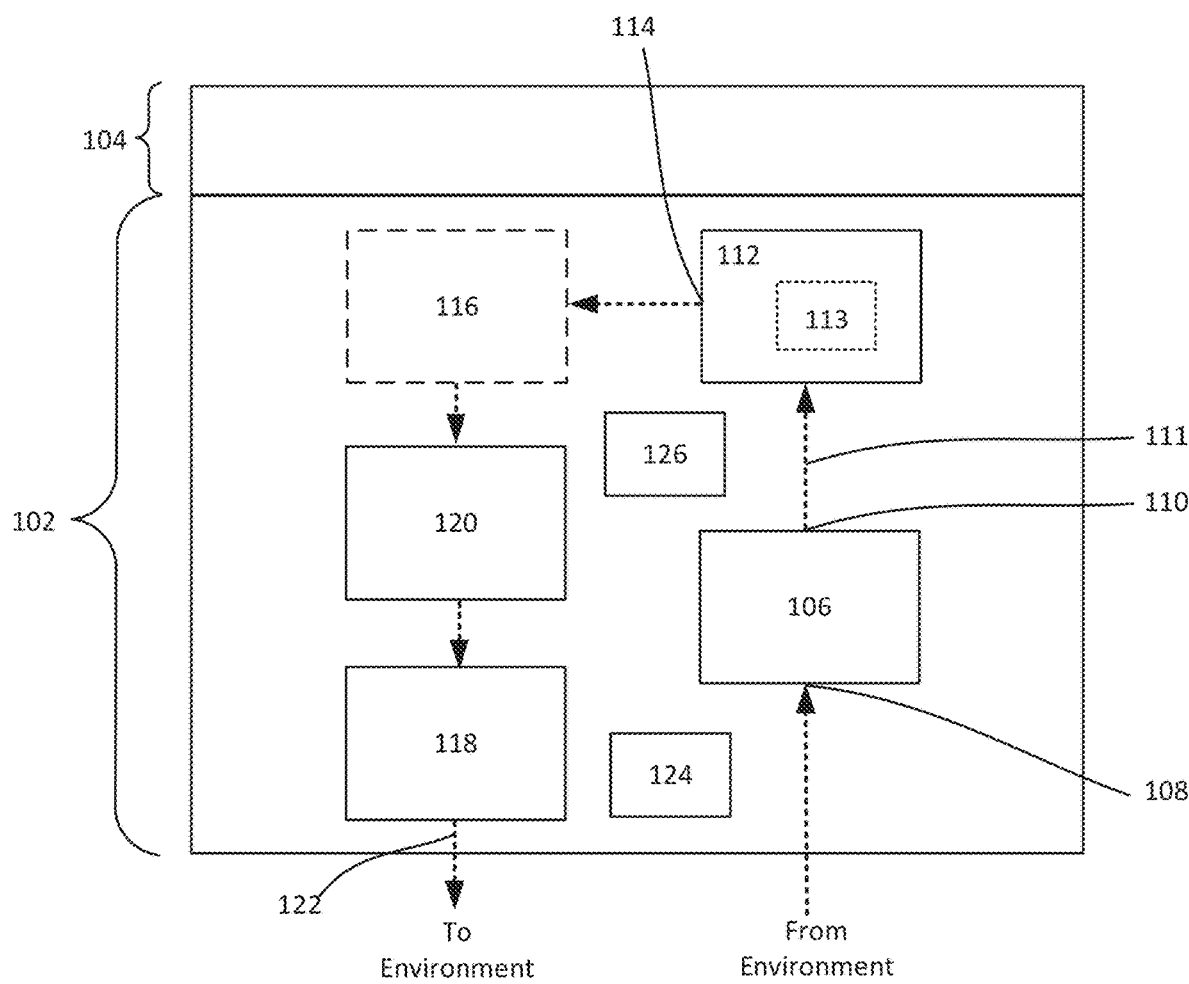
FIG. 2 is a block diagram of another example of a disinfection device with a fan upstream of a filter, consistent with the present disclosure.

Discharge outlet 122 may be fluidly coupled to the filter 118 in any suitable manner. For example, the discharge outlet may be fluidly coupled to the fan 120 and discharge the filtered exhaust stream, e.g., into the environment surrounding disinfection device 100. In the embodiment of FIG. 1 the discharge outlet 122 is fluidly coupled (e.g., directly or indirectly) with and located downstream of the fan 120. In the embodiment of FIG. 2, the discharge outlet 122 is fluidly coupled with and located downstream of the filter 118.

As noted above in the first flow condition the lid 104 is in the closed position, only a first flow path is present through disinfection device 100 and the resistance to gas flow (first gas flow resistance) through disinfection device 100 is high. In contrast when the lid 104 is open, a second flow path is also present through disinfection device 100 and the resistance to gas flow (second gas flow resistance) through disinfection device 100 is low, relative to the first gas flow resistance. In the first flow condition (i.e., when the first gas flow resistance is imposed) the fan 120 is configured to generate a first (relatively high) static pressure and to cause gas to flow through the disinfection device 100 at a first (relatively low) flow rate. Conversely in the second flow condition (i.e., when the second gas flow resistance is imposed), the fan 120 is configured to generate a second (relatively low) static pressure and to cause gas to flow through the disinfection device 100 at a second (relatively high) flow rate.

In disinfection device 100 the first flow path extends from the inlet 108, through sanitizing gas supply 106, through outlet 110, through sanitization chamber 112, through optional exhaust channel 116 (when present), through filter 118 (when present), through fan 120, and through distribution outlet 122. The first flow path includes a restricted portion, i.e., a portion through which the resistance to gas flow is relatively high, as compared to the resistance to gas flow through other portions of the first flow path. The restricted portion of the first flow path may be defined by one or more parts of disinfection device 100 that form part of the first flow path. For example, the inlet 108, outlet 110, and/or passageways within sanitizing gas supply 106 may form all or at least a portion of the restricted portion of the first flow path.

The second flow path in disinfection device 100 extends from a chamber opening of sanitization chamber 112, through at least a portion of the sanitization chamber 112, through exhaust port 114, through optional exhaust channel 116 (when present), through filter 118 (when present), through fan 120, and through distribution outlet 122. The cross sectional area of the passages within the second flow path may be relatively large compared to the cross sectional area of the passage(s) in the restricted portion of the first flow path. Thus, the second flow path may be relatively unrestricted relative to the first flow path.

In embodiments sanitizing gas supply 106, inlet 108 and/or outlet 110 may include respective supply, inlet, and outlet passageways that form at least a portion of the restricted portion of the first flow path. The cross sectional area of one or more of such passageways may be relatively small compared to the cross sectional of the inlet to fan 120 and other passageways forming part of the first flow path. For example, the inlet 108 and/or outlet 110 may include at least one circular passageway with a first diameter and the fan intake may have a circular fan intake with a second diameter that is larger than the first diameter. The first diameter may be less than or equal to about 10 mm (e.g., less than or equal to about 5 mm, less than or equal to about 2.5 mm, less than or equal to about 2.0 mm, or even less than or equal to about 1 mm), and the second diameter may be that is greater than 10 mm (e.g., greater than or equal to about 15 mm, greater than or equal to about 20 mm, greater than or equal to about 25 mm, greater than or equal to about 30 mm, or more). Put differently, in embodiments the second diameter may be at least about 20% larger (e.g., at least about 50%, 100%, 200%, 300%, 400%, 500%, 750%, 1000%, or even 1500%) than the first diameter. In specific embodiments, the inlet 108 includes an inlet passageway with a first diameter of greater than 0 to 2.5 mm, and the intake to fan 120 has a second diameter of greater than or equal to about 30 mm.

The foregoing discussion describes example differences in the relative diameter of the fan intake and the diameter of passageways in the inlet 108, sanitizing gas supply 106, and outlet 110, implying that the inlet and outlet passageways have a circular cross section. While such a cross section is useful, the shape of the passageways in the first flow path (including the passageways within the sanitizing gas supply 106, inlet 108, outlet 110, and the inlet to fan 120 need not be circular. Indeed the passageways included in the first flow path may have any suitable cross sectional shape, such as a geometric (e.g., circular, triangular, quadrilateral, etc.) or irregular shape. In such instances, at least part of the restricted portion of the first flow path may have a first cross sectional area that is less than a second cross sectional area of the fan intake.

In the first flow condition fan 120 is configured to generate a first static pressure and to cause gas to flow at a first flow rate through the disinfection device 100. In contrast in the second flow condition fan 120 is configured to generate a second static pressure and cause gas to flow at a second flow rate through the disinfection device 100, wherein the second static pressure is less than the first static pressure and the second flow rate is greater than the first flow rate. In embodiments the second flow rate is at least 15% (e.g., at least 25%, at least 50%, at least 75%, at least 100%, at least 150%, at least 200%, at last 300%, at least 400%, or even at least 500%) greater than the first flow rate. In specific embodiments the second flow rate is at least 400% or even at least 500% greater than the first flow rate.

Figure 5:
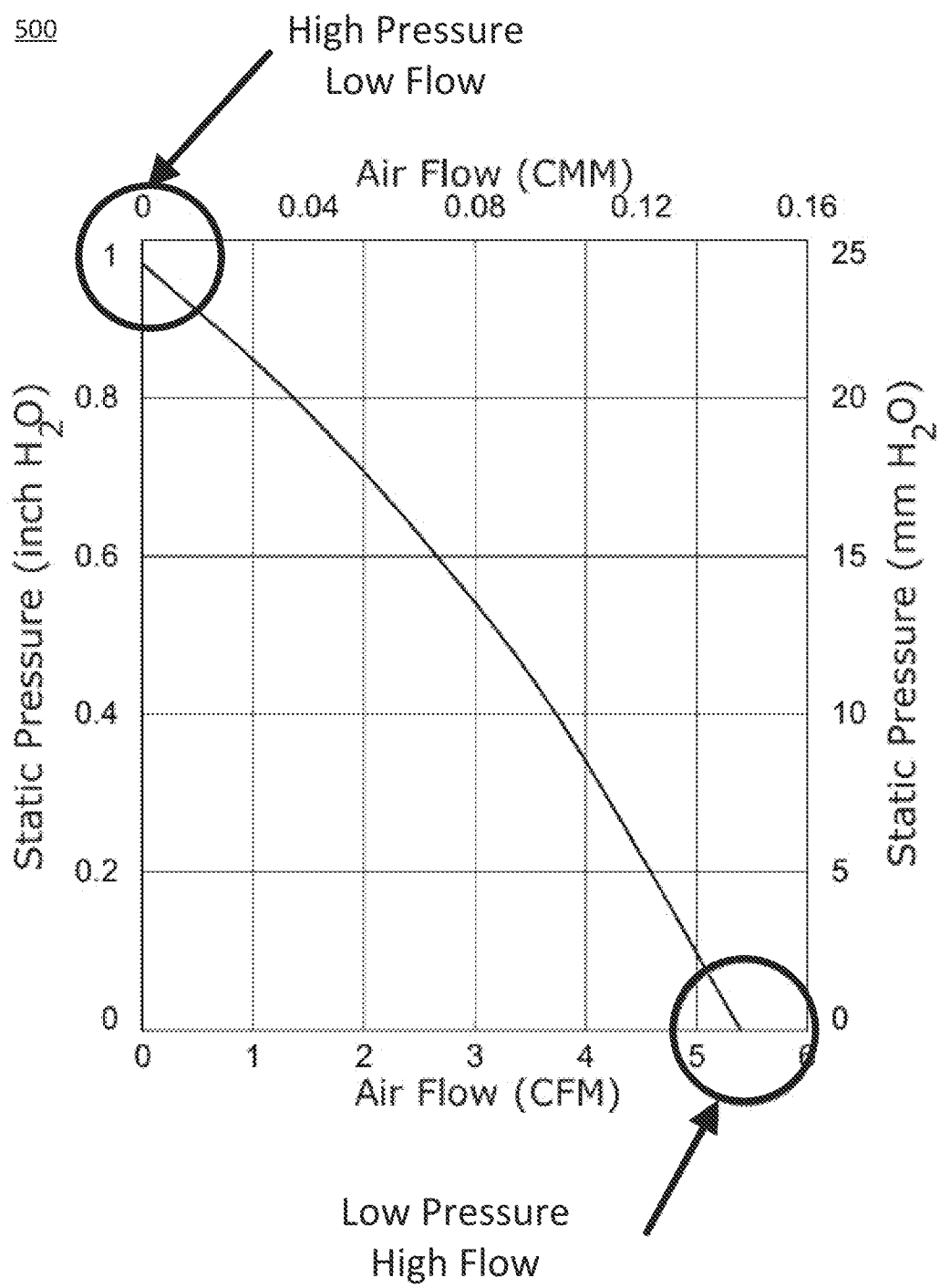
FIG. 5 is a graph that plots static pressure (in inches of $H_2O$ water or millimeters (MM) of $H_2O$) versus air flow (in cubic meters per minute (CMM) or cubic feet per minute (CFM)).

To illustrate this concept reference is made to FIG. 5, which is one example of a plot 500 of static pressure versus air flow for a fan consistent with the present disclosure. It is noted that the values of static pressure and air flow in FIG. 5 are for the sake of example only, and the fans described herein are not limited thereto. As illustrated in FIG. 5, when resistance to gas flow is high (first gas flow resistance), the fan 120 is configured to produce a first (relatively high) static pressure—e.g., ≥about 0.5 inches $H_2O$ (≥12.5 millimeters (mm) $H_2O$)—and cause gas to flow at a first (relatively low) flow rate—e.g., ≤about 3 cubic feet per minute (CFM) (≤0.04 cubic meters per minute (CMM) or about 85 liters per minute (LPM)). In contrast when resistance to gas flow is low (second gas flow resistance), the fan 120 is configured to produce a second (relatively low) static pressure—e.g., ≤about 0.4 inches $H_2O$ (≤10 millimeters (mm) $H_2O$), and cause gas to flow at a second (relatively high) flow rate—e.g., ≥about 3.8 CFM (≥0.10 CMM or about 108 LPM).

The first flow rate may range from greater than 0 to less than or equal to about 85 LPM, such as greater than 0 to less than or equal to about 50 LPM, greater than 0 to less than or equal to about 25 LPM, greater than 0 to less than or equal to about 10 LPM, greater than 0 to less than or equal to about 1 LPM, greater than 0 to less than or equal to about 0.5 LPM, or even greater than 0 to less than or equal to about 0.2 LPM. In embodiments, the first flow rate is greater than 0 to less than or equal to about 1 LPM, such as greater than 0 to less than or equal to about 0.5 LPM, or even greater than 0 to less than or equal to about 0.2 LPM. In specific non-limiting embodiments, the first flow rate is greater than 0 but less than or equal to about 0.2 LPM. In those or other embodiments, the second flow rate may be greater than or equal to about 100 LPM, such as greater than or equal to about 110 LPM, greater than or equal to about 120 LPM, greater than or equal to about 130 LPM, greater than or equal to about 140 LPM, or even greater than or equal to about 150 LPM. For example, the first flow rate range from greater than 0 to less than 1 LPM (e.g., greater than 0 but less than 0.2 LPM), and the second flow rate may be greater than or equal to about 100 LPM (e.g., greater than or equal to about 100 LPM, 125 LPM, or even 150 LPM). In specific non-limiting embodiments, the first flow rate ranges from greater than 0 to less than or equal to about 0.2 LPM, and the second flow rate is greater than or equal to about 150 LPM.

Disinfection device 100 further includes a controller 124 and a user interface 126. Controller 124 is generally configured to control the operation of the disinfection device 100, e.g., during the performance of disinfection operations and termination operations described herein. User interface 126 is generally configured to enable a user to initiate performance of a disinfection operation with the disinfection device, and/or to terminate a disinfection operation that is currently in process. For example, user interface may include one or more buttons, switches, or other interactive elements that allow a user to initiate a disinfection operation. In response to an input from a user, the user interface 126 may produce and send an initiation signal to controller 124. In response to the initiation signal, the controller 124 may initiate the performance of a disinfection operation.

During a disinfection operation controller 124 may cause sanitizing gas supply 106 and fan 120 to operate. Controller 124 may permit or deny operation of the sanitizing gas supply 106 based at least in part on the position of lid 104, which may be determined by controller 124 in any suitable manner. For example, disinfection device 100 may include a lid position sensor (not shown) which is configured to sense a position of lid 104 and to output a lid position signal to controller 124. Controller 124 may determine whether lid 104 is in the closed position or the open position based at least in part on the lid position signal. When controller 124 determines that the lid is in the closed position, it may permit execution of disinfection operations consistent with the present disclosure. When controller 124 determines that lid 104 is in the open position, however, it may prevent the initiation of a disinfection operation, e.g., by preventing operation of the sanitizing gas supply 106. In such instances controller 124 may also cause disinfection device 100 to perform one or more termination operations consistent with the present disclosure.

As noted above controller 124 may permit execution of a disinfection operation when the lid 104 is closed. During such an operation controller 124 may cause sanitizing gas supply 106 (e.g., an ozone generator) and fan 120 to operate. More specifically, controller 124 may cause sanitizing gas supply 106 to provide a sanitizing gas, and cause fan 120 to operate in the first flow condition. In that condition fan 120 will generate a first static pressure within disinfection device 100, which will cause gas to flow through the first flow pathway at a first flow rate (e.g., less than or equal to about 1 LPM, or even less than or equal to about 0.2 LPM), as previously described. As a result, sanitizing gas will flow from the sanitizing gas supply 106 into sanitization chamber 112, where it can sanitize an article 113 contained therein.

In some embodiments controller 124 causes the sanitizing gas supply 106 (e.g., an ozone generator) to supply sanitizing gas continuously or in accordance with a pre-determined gas delivery profile. For example, controller 124 may cause sanitizing gas supply 106 to generate or otherwise provide sanitizing gas continuously over a sanitization cycle, i.e., for the entire duration of a sanitizing cycle. Alternatively, controller 124 may implement a gas delivery profile that causes sanitizing gas supply 106 to supply sanitizing gas in accordance with the parameters defined therein. For example, the gas delivery profile may cause sanitizing gas supply 106 to supply sanitizing gas at a fixed or variable intervals, wherein said intervals range from less than or equal to 1 second to greater than or equal to 5 minutes. In embodiments, gas delivery profile is configured to cause the sanitizing gas supply 106 to supply sanitizing gas at fixed intervals within a range of from about 1 second to about 120 seconds, such as from about 1 second to about 60 seconds, from about 1 second to 45 seconds, or even from about 1 second to about 30 seconds. In embodiments the gas delivery profile causes the sanitizing gas supply 106 to supply sanitizing gas at a 20 to 30 second interval over the course of a disinfection operation, such as at a 25 second interval over the course of a disinfection operation.

During the performance of a disinfection operation controller 124 may monitor the position of lid 104 in any suitable manner, such as by monitoring a lid position signal received from a lid position sensor as discussed above. If lid 104 is moved from the closed position to the open position while a disinfection operation is in process, controller 124 may cause disinfection device 100 to perform a termination operation consistent with the present disclosure.

During a termination operation controller 124 may disable operation of the sanitizing gas supply 106, while causing or allowing fan 120 to continue to operate. Because the lid 104 is in the open position, fan 120 will operate in the second flow condition and generate a second static pressure within disinfection device 100, causing external air and gas within the sanitization chamber 112 (including sanitizing gas) to flow through the second flow pathway at a second flow rate as previously described. Because the second flow rate is relatively high, copious amounts of external air will be drawn into the sanitization chamber 112 and through the exhaust port 114. This will dilute and rapidly evacuate the sanitizing gas through the exhaust port. During the termination operation, the controller 124 may cause the fan 120 to operate for an exhaust period that may be selected to ensure that all or substantially all of the sanitizing gas is removed from the sanitization chamber 112 and passed through filter 118, as discussed above. The exhaust period may be less than or equal to about 20, about 10, about 5, about 1, about 0.5, or even about 0.1 seconds.

In FIG. 1, fan 120 is located downstream of the filter 118. While that position is preferred, it is not required and fan 120 may be positioned at any suitable location. In that regard reference is made to FIG. 2, which depicts another example of a disinfection device consistent with the present disclosure. Disinfection device 200 includes the same components as disinfection device 100, and so such components are not described again in the interest of brevity. In disinfection device 200, however, fan 120 is positioned upstream of filter 118 and downstream of exhaust channel 116, as shown in FIG. 2. As such, fan 120 may be configured to draw (or suck) an unfiltered exhaust stream from exhaust port 114 and blow (or push) the unfiltered exhaust stream through filter 118 (if present) and discharge outlet 122.

Figure 3:
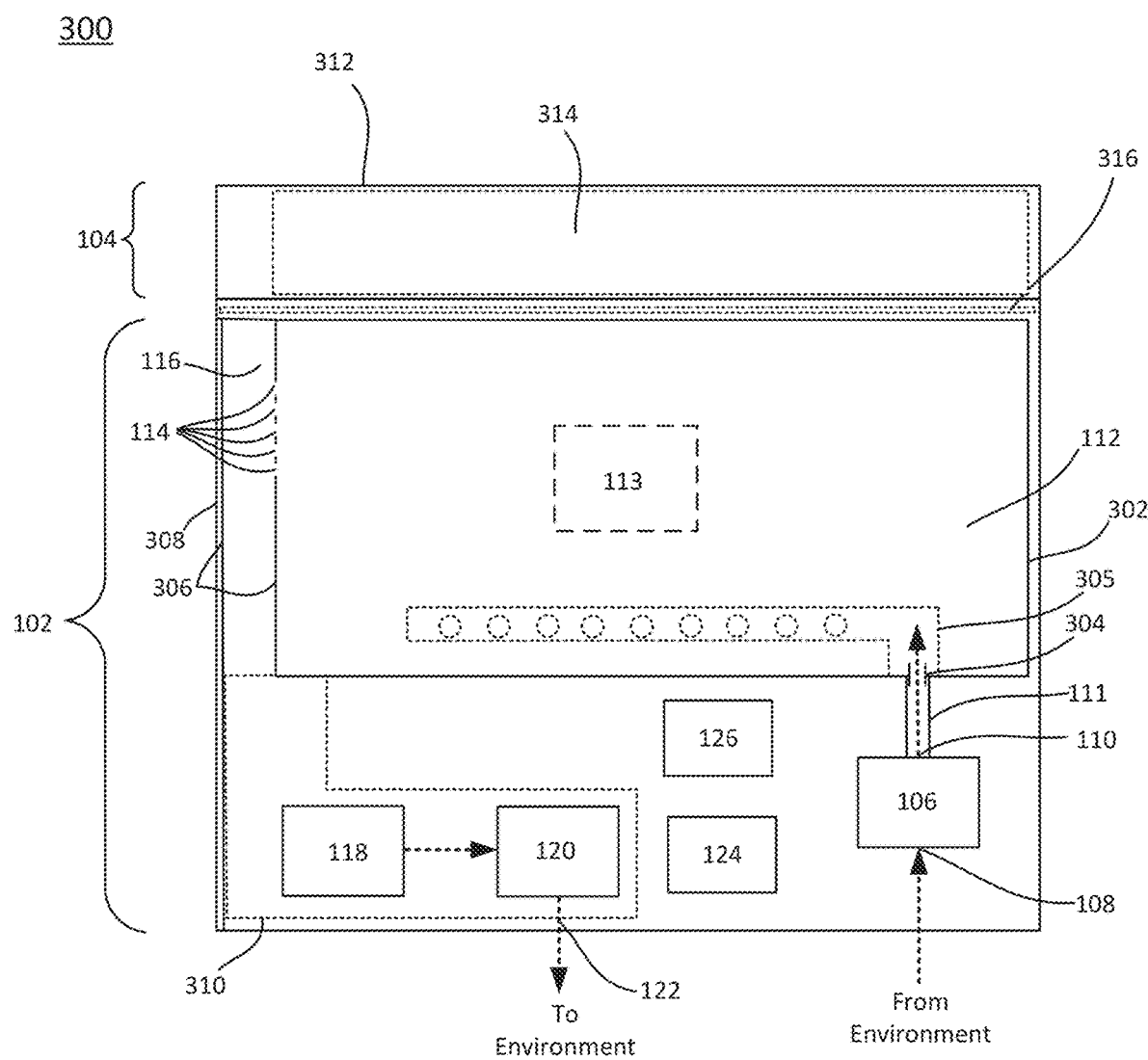
FIG. 3 is a block diagram of another example of a disinfection device with a fan downstream of a filter, consistent with the present disclosure.

FIG. 3 is a block diagram of another example of a disinfection device 300 consistent with the present disclosure. As the nature and function of many of the components of disinfection device 300 are the same as described above in connection with FIGS. 1 and 2, such components are not described again in detail.

As shown, disinfection device 300 includes a base 102 and a lid 104 that is movable between a closed position and an open position. Disinfection device 300 further includes a sanitizing gas supply 106 (e.g., an ozone generator) with an inlet 108 and an outlet 110. The outlet 110 is fluidly connected to a sanitization chamber 112 by a distribution line 111. The sanitization chamber 112 includes a cavity defined at least in part by a chamber wall 302, wherein the cavity is configured to contain at least one article 113 therein. Disinfection device 300 further includes at least one exhaust port 114. In this case the at least one exhaust port 114 is in the form of one or more openings formed through a side wall of sanitization chamber 112, but it should be understood that the exhaust port(s) 114 may be located elsewhere. For example, the exhaust port(s) may be located a bottom wall of sanitization chamber 112, a side wall of sanitization chamber 112, within lid 104, or a combination thereof.

An exhaust channel 116 is positioned downstream of the at least one exhaust port 114. The exhaust channel 116 includes an exhaust passageway that has a proximal end and a distal end. The proximal end of the exhaust passageway is in fluid communication with the at least one exhaust port 114, and the distal end of the exhaust passageway is in fluid communication with a filter 118. Filter 118 is in fluid communication with a fan 120, which in turn is in fluid with a distribution outlet 122. As discussed previously the filter 118 is configured to receive an unfiltered exhaust stream that contains a first amount of a sanitizing gas, and produce a filtered exhaust stream that contains a second amount of the sanitizing gas that is less than the first amount of the sanitizing gas. The distribution outlet 122 is configured to receive and convey the filtered exhaust stream, e.g., to the environment surrounding disinfection device 300.

As further shown in FIG. 3, sanitization chamber 112 includes a chamber inlet 304 that is configured to fluidly couple the outlet 110 to a cavity within the sanitization chamber 112. In embodiments, the chamber inlet 304 is configured to couple directly to the outlet 110 of sanitizing gas supply. Alternatively and as shown in FIG. 3, a distribution line 111 may be used to couple the chamber inlet 304 with the outlet 110. In such instances the distribution line 111 may by the form of a hose or channel having a distribution passageway that extends from a proximal end of the distribution line 111 to a distal end of the distribution line. The proximal end of the distribution line 111 may be coupled to the outlet 110, and the distal end of the distribution line 111 may be coupled to the chamber inlet 304. The nature of the connection between the chamber inlet and the distribution line 111 (or the outlet 110) is not limited, and the chamber inlet 304 may be configured to support any desired type of connection. For example the chamber inlet 304 may include be in the form of a barb that is configured to fit within or over the distal end of the distribution line 111 and/or outlet 110. In such instances the chamber inlet 304 may include an inlet opening that provides a fluid passageway into the sanitization chamber 112.

In the embodiment of FIG. 3 the chamber inlet 304 is shown as being formed through a bottom of sanitization chamber 112, with a distal end of the chamber inlet 304 disposed within an interior of sanitization chamber 112 (i.e., within a cavity thereof). Such positioning and configuration are not required and chamber inlet 304 may be positioned and configured differently. For example, chamber inlet 304 may be positioned at any suitable location, such as through one or more walls of sanitization chamber 112, e.g., a bottom wall, a side wall, or a combination thereof. Chamber inlet 304 may also be provided in part of lid 104 that forms a top of sanitization chamber 112 when the lid 104 is the closed position. The number of chamber inlets 304 is also not limited, and more than one chamber inlet 304 may be used. For example, in embodiments the disinfection devices described herein may include at least 1, 2, 3, 4, 5, or more chamber inlets 304, with a corresponding number of distribution lines 111 and/or outlets 110.

Chamber inlet 304 may also be coupled to optional diffuser 305. When used, optional diffuser 305 may include a passageway with a proximal end fluidly coupled to chamber inlet and a distal end. In embodiments the distal end may be open and fluidly coupled to sanitization chamber 112. Alternatively or additionally, optional diffuser 305 may include a passageway defined by at least one wall, and one or a plurality of openings formed through the at least one wall. That concept is shown in FIG. 3, which depicts optional diffuser 305 as including a plurality of openings. In any case, optional diffuser may function to introduce sanitizing gas at a desired location within the sanitization chamber, e.g., to facilitate the flow and contact of sanitizing gas into and/or around an article 113.

As further shown in FIG. 3, exhaust channel 116 is located downstream of exhaust port(s) 114 and includes one or more exhaust channel walls 306. The exhaust channel walls 306 generally define a passageway that extends within exhaust channel 116. In embodiments the exhaust channel 116 and sanitization chamber 112 are discrete elements that are fluidly connected to one another, e.g., via the at least one exhaust port. In other embodiments such components are integrally formed or otherwise coupled to one another such that an outward facing surface of at least one sanitization chamber wall 302 is an inward facing surface of at least one the exhaust channel walls 306. In such instances another of the exhaust channel walls 306 may be defined by an inward facing surface of a base wall 308 of base 102.

In embodiments the sanitization chamber 112 and exhaust channel 116 may be integrally formed or otherwise coupled to one another to form a chamber insert. In such instances the base 102 may include at least one base wall 308, wherein the base wall 308 defines a base cavity (not labeled). The base cavity is configured to receive at least a portion of the chamber insert and other components (e.g., sanitizing gas supply 106, filter 118, fan 120, etc.) therein. In such instances, one or more of the exhaust channel walls 306 may be separate from base wall 308 and from the sanitization chamber wall 302. Alternatively, the chamber insert may be configured such that the exhaust channel 116 and the sanitization chamber 112 include at least one common wall. For example and as described previously, an outward facing surface of the chamber wall 302 may form an inward facing surface of at least one exhaust channel wall 306. In such instances the base wall 308 may be discrete from the exhaust channel wall(s) 306.

Disinfection device 300 may also include an optional filter chassis 310. When used, filter chassis 310 may be configured to receive and support filter 118 therein. For example, when filter 118 is in the form of a filter cartridge, filter chassis 310 may include a filter receptacle that is configured to receive the filter cartridge therein. Filter chassis 310 may also be configured to provide at least a portion of a fluid connection between exhaust channel 116 and filter 118 or, more specifically, to an inlet of a filter cartridge disposed in the filter receptacle. For example, filter chassis 310 may include a filter inlet passageway having a proximal end that is configured to provide a fluid connection between exhaust channel 116 and an inlet of a filter cartridge within the filter receptacle. In embodiments, the filter chassis 310 also includes a filter outlet passageway that is configured to provide a fluid passageway between the filter 118 (or, more specifically, an outlet of a filter cartridge) and the fan 120. When filter chassis 310 is not used, the filter 118 may be configured to fluidly couple to the exhaust channel 116 and the fan 120 in any suitable manner Filter chassis 310 may also form at least part of a support for fan 120 and, in some embodiments, fan 120 is located within filter chassis 310.

As discussed above disinfection device 300 includes a lid 104 that is movable between an open position and a closed position. In the closed position, at least a portion of the lid 104 blocks a chamber opening that provides access to sanitization chamber 112. The lid 104 may also form a seal with a peripheral surface (e.g., a rim) of the chamber opening when it is in the closed position, so as to prevent leakage of sanitizing gas from sanitization chamber 112. In embodiments and as shown in FIG. 3, lid 104 may include a lid wall 312. The exterior of the lid wall 312 may function to define at least a portion of the outer shape of lid wall 312. In such embodiments when lid 104 is in the closed position, sanitization chamber 112 may include an upper portion defined at least in part by the interior of the lid wall 312 and a lower portion that is located within the base 102.

Alternatively, in embodiments lid 104 includes an optional lid insert 314. In such instances the lid wall 312 may define a lid cavity that is configured to receive at least a portion of the lid insert 314 therein. The lid insert may have a peripheral surface that is configured to form a seal with a peripheral surface (e.g., a rim) of the chamber opening of the sanitization chamber when the lid 104 is in the closed position. A sealing member such as a gasket may be provided around a peripheral surface of the lid insert to facilitate the formation of a seal between the peripheral surface of the lid insert and a peripheral surface of the sanitization chamber.

Disinfection device 300 may also include an optional indicator 316, which may form part of or be discrete from controller 124 and/or user interface 126. The indicator 316 can be a liquid crystal display (LCD), an organic light emitting diode (OLED) display, one or more light emitting diodes (LEDs) that illuminate to display a status, a light bar/pipe, combinations thereof, and the like. When used, indicator 316 can be configured to indicate a status of the disinfection device 300. For example, indicator 316 may be configured to indicate that a sanitizing or termination operation is being conducted by disinfection device 300. In embodiments, indicator 316 is or includes a light bar/pipe that is configured display a first color when a sanitizing operating is being conducted, and to display a second color when a termination operation is being conducted, wherein the first and second colors are different. Indicator 316 may also be configured to provide a visual indicator of the time remaining for a disinfection operation or a termination operation to complete.

Figure 4:
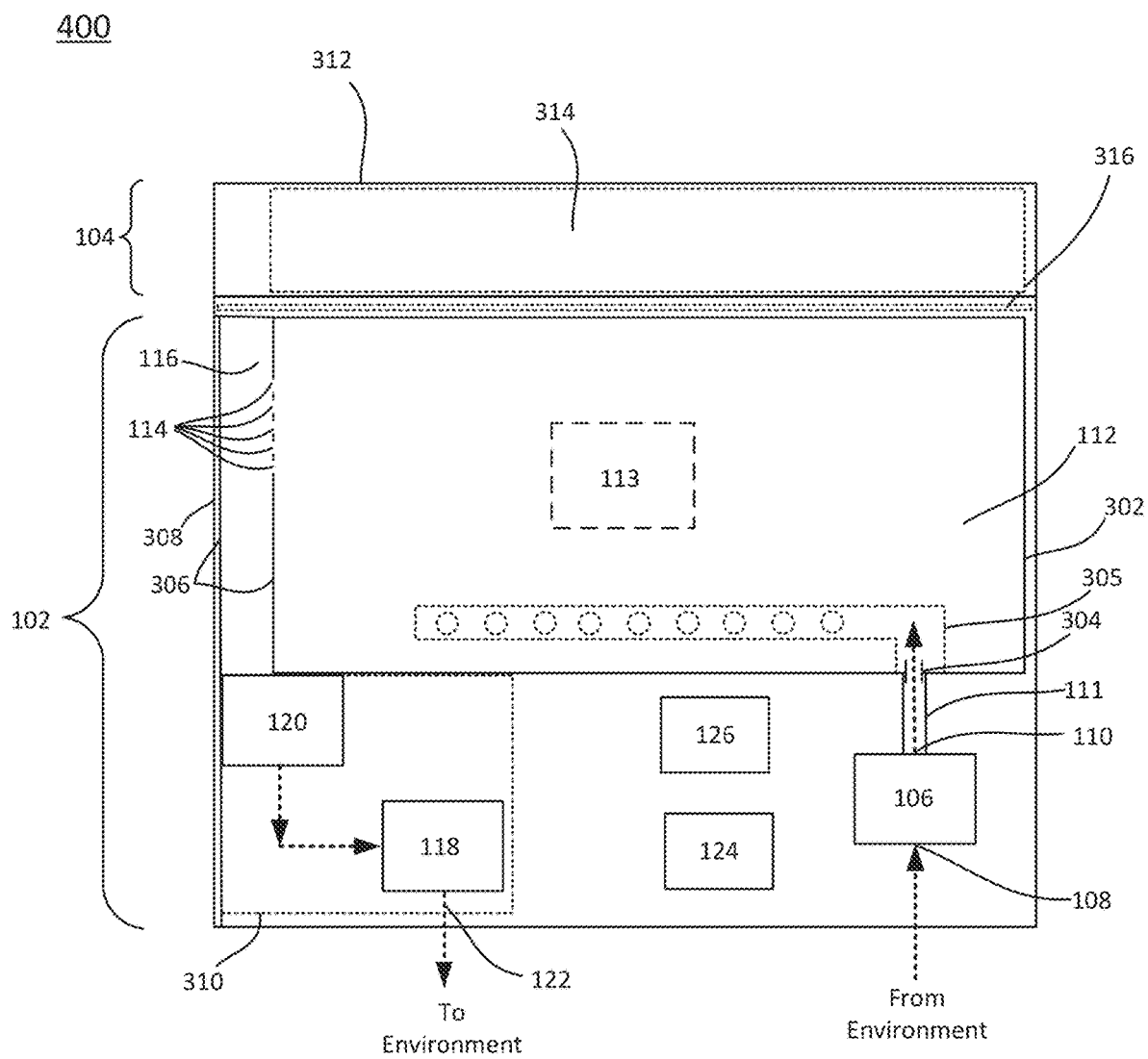
FIG. 4 diagram of another example of a disinfection device consistent with a fan upstream of a filter, with the present disclosure.

Like disinfection device 100, in disinfection device 300 fan 120 is located downstream of the filter 118. While that position is preferred, it is not required and fan 120 may be positioned at another suitable location. In that regard reference is made to FIG. 4, which depicts another example of a disinfection device consistent with the present disclosure. Disinfection device 400 includes the same components as disinfection device 300, and so such components are not described again in the interest of brevity. In disinfection device 400, however, fan 120 is positioned upstream of filter 118 and downstream of exhaust channel 116, as shown in FIG. 4. As such, fan 120 may be configured to draw (or suck)

an unfiltered exhaust stream from exhaust port 114 and blow (or push) the unfiltered exhaust stream through filter 118 (if present) and discharge outlet 122.

Figure 6A:
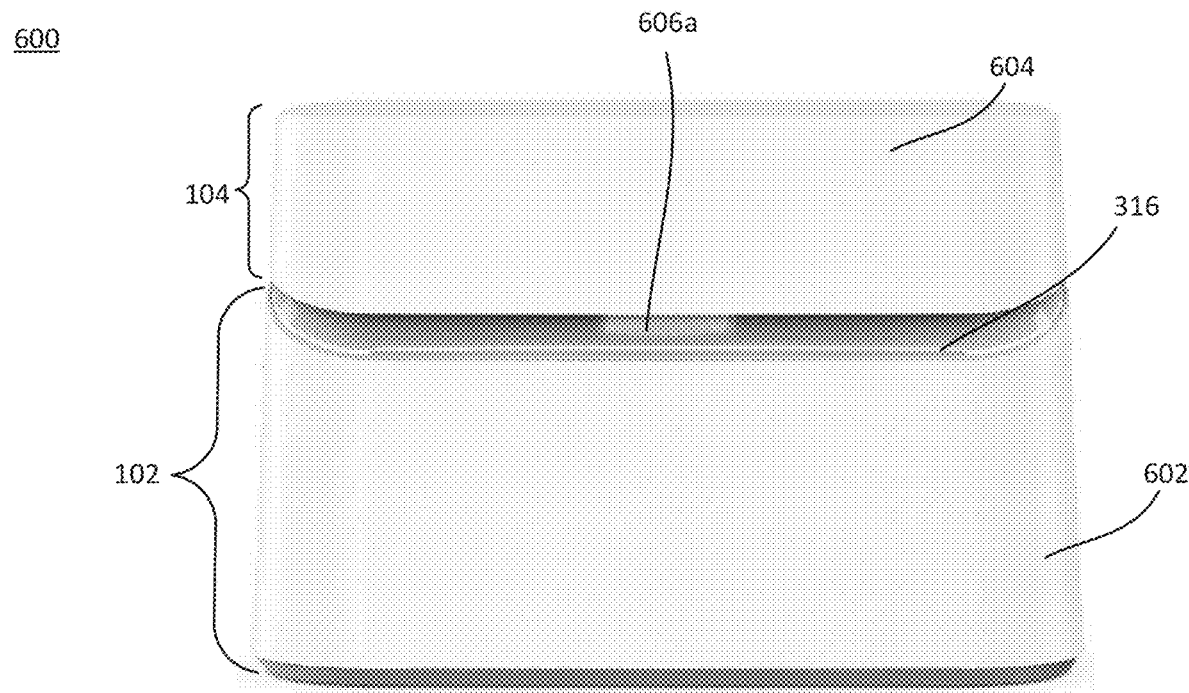
FIG. 6A is a front view of one example of a disinfection device consistent with the present disclosure, with a closed lid.
Figure 6B:
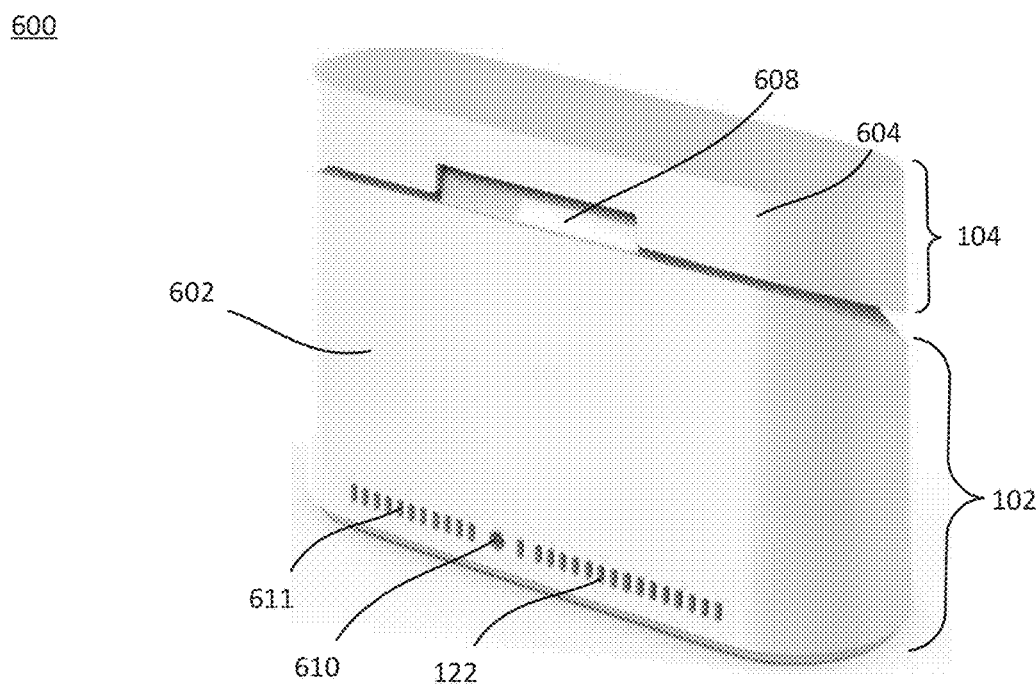
FIG. 6B is a rear perspective view of the disinfection device of FIG. 6A, with a closed lid.

FIGS. 6A-6F depict various view of another example of a disinfection device consistent with the present disclosure. The nature and function of many of the elements of disinfection device 600 are the same as described above in connection with FIGS. 1-4, and so are not re-described in detail in the interest of brevity. As shown, disinfection device 600 includes a base 102 and a lid 104. The base 102 has a lower housing that includes a base outer wall 602, and the lid has an upper housing that includes a lid outer wall 604. Like the other embodiments, lid 104 is movable between an open and a closed position, as best shown by FIGS. 6A and 6B (closed position) and FIGS. 6C, 6E, and 6F (open position). Disinfection device 600 and further includes a lower catch 606a and upper catch 606b, which are configured to retain lid 104 in a closed position, as discussed further below.

In this embodiment lid 104 is coupled to base 102 by a hinge 608 and a hinge pin 609, around which lid 104 rotates as it is moved between the closed and open positions. Although such a configuration is preferred, it is not required and lid 104 may be coupled to base 102 in any suitable manner. For example, lid 104 may be configured to detachably couple with base 102, to slide relative to an axis extending through sanitization chamber 112, or in any other suitable manner that allows disinfection device 100 to transition between an closed position (in which the lid 104 closes sanitization chamber 112) and an open position (in which an open end of the sanitization chamber 112 is accessible).

Disinfection device 600 further includes a sanitizing gas supply 106 comprising an inlet 108 and an outlet 110 (not shown). In this embodiment sanitizing gas supply 106 is or includes an ozone generator that is configured to generate ozone gas, e.g., from air. In embodiments, the sanitizing gas supply 106 is or includes an ozone generator that is configured to generate ozone gas, e.g., via corona discharge. To that end and as best shown in FIGS. 6B and 6F, disinfection device 600 may include a power connector 610 and a plurality of inlet openings 611. Power connector 610 is configured to connect disinfection device 600 to a source of electric power, such as AC or DC mains power. Alternatively, power connector 610 may be omitted and disinfection device 600 may be powered via an alternative energy source, such as one or more batteries, solar panels, combinations thereof, and the like. In any case, power supplied to disinfection device 600 may be used by the ozone generator in sanitizing gas supply 106 to generate ozone from air received via inlet 108, which is fluidly coupled to inlet openings 611.

As best shown in FIG. 6F, disinfection device 600 includes a distribution line 111 that fluidly couples the outlet 110 of sanitizing gas supply 106 to sanitization chamber 112. More specifically, distribution line 111 includes a proximal end fluidly (or directly) coupled to the outlet 110 of sanitizing gas supply 106, and a distal end coupled to a proximal end of a chamber inlet 304 that is in fluid communication with sanitization chamber 112. The chamber inlet 304 includes a passageway that extends at least partially through a wall (e.g., a bottom wall, a side wall, or a combination thereof) of the sanitization chamber 112. In this embodiment and as best shown in FIGS. 6D and 6F, the chamber inlet 304 extends through the bottom of sanitization chamber 112, such that proximal end of the chamber inlet 304 is below the bottom of sanitization chamber 112 and the distal end of the chamber inlet 304 is in fluid communication with the sanitization chamber 112. In embodiments, the distal end of the chamber inlet 304 is disposed above a surface of the bottom of the sanitization chamber 112. Alternatively or additionally, in some embodiments the distal end of the chamber inlet 304 is fluidly (or directly) coupled to an optional diffuser that is located within sanitization chamber 112.

Figure 6C:
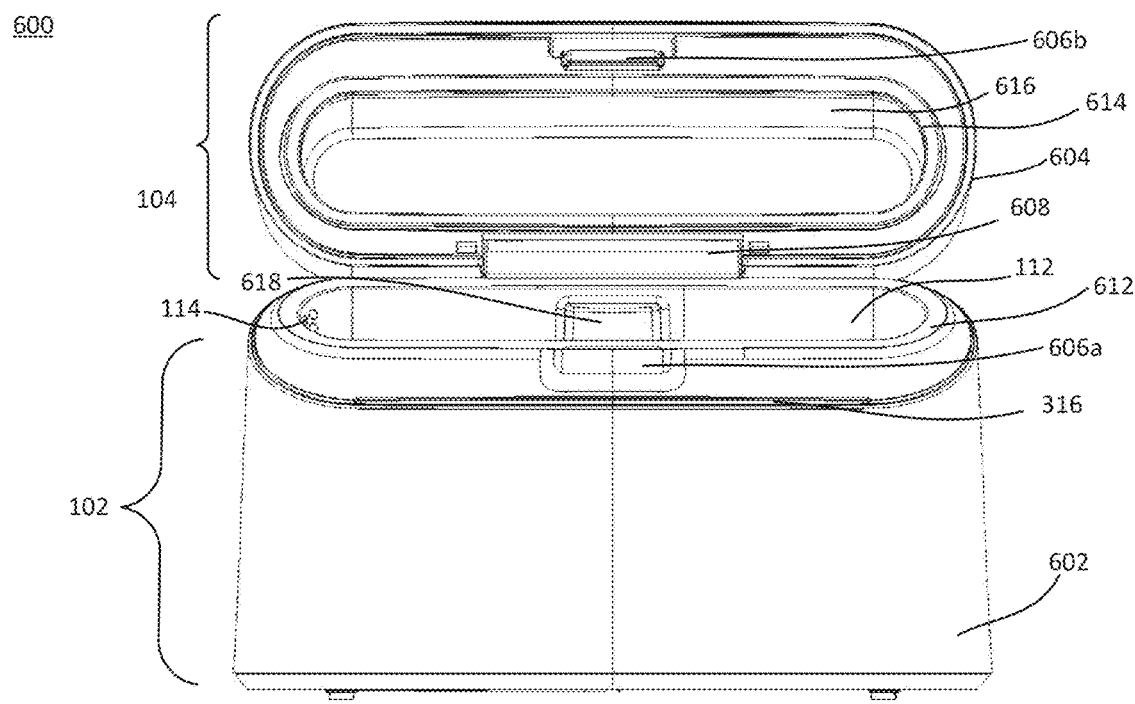
FIG. 6C is a front view of the disinfection device of FIG. 6A, with an open lid.
Figure 6D:
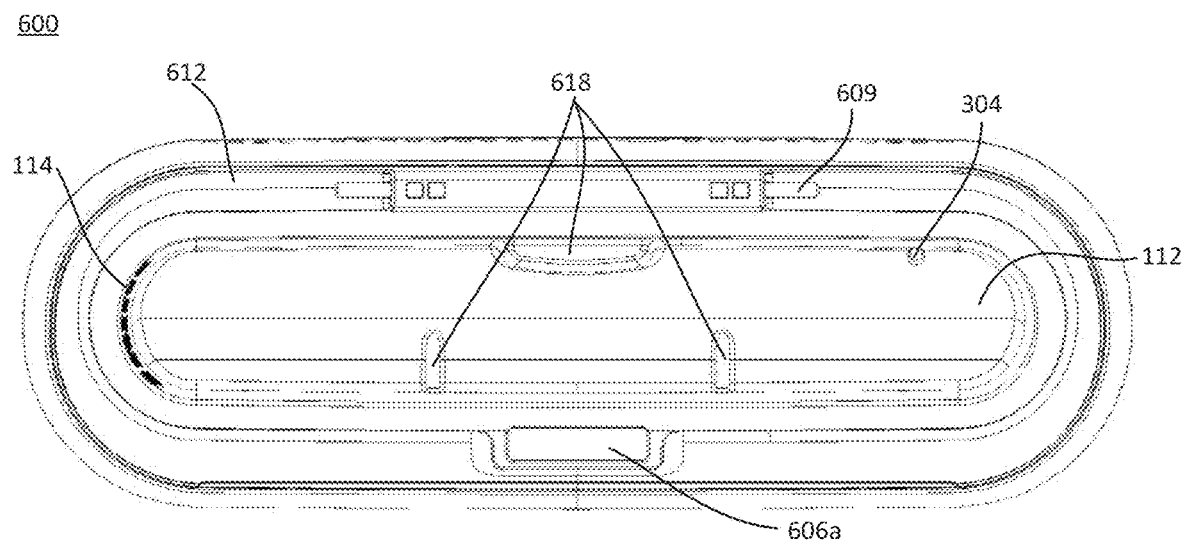
FIG. 6D is a top down view of the disinfection device of FIG. 6A, with the lid removed for clarity.
Figure 6E:
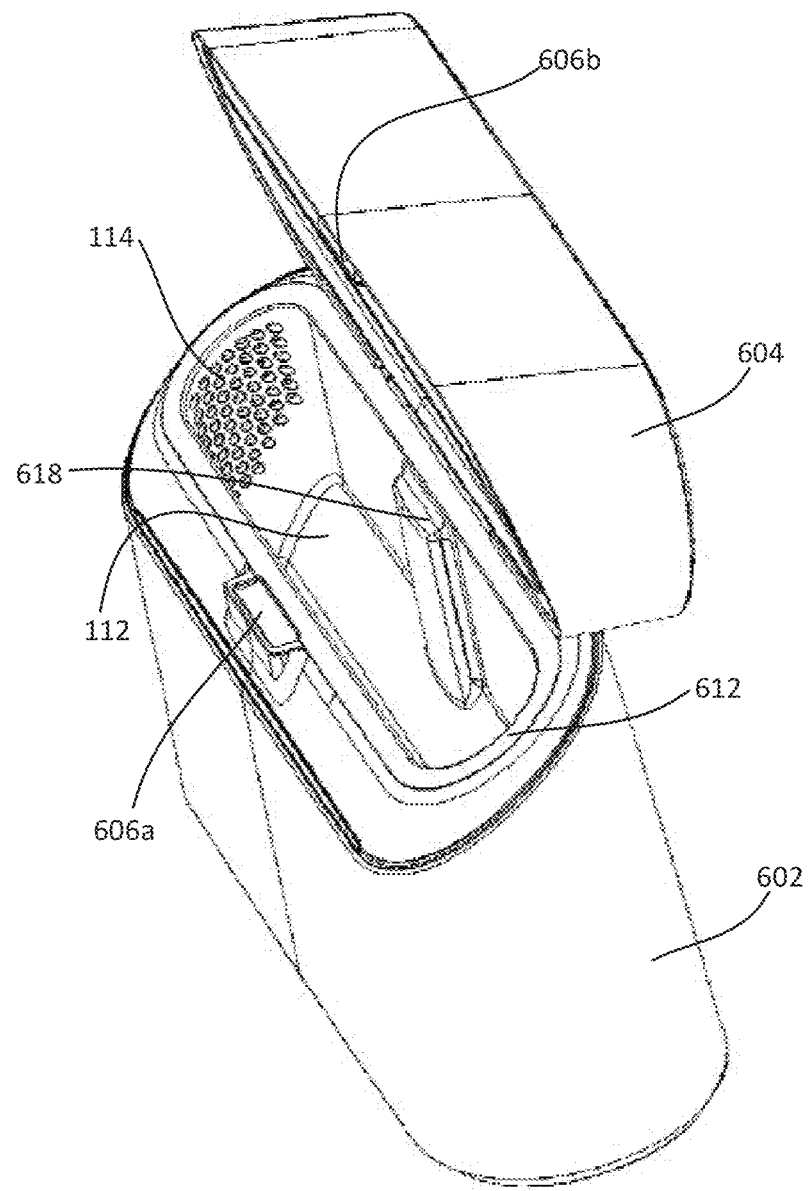
FIG. 6E is a side perspective view of the disinfection device of FIG. 6A, with an open lid.
Figure 6F:
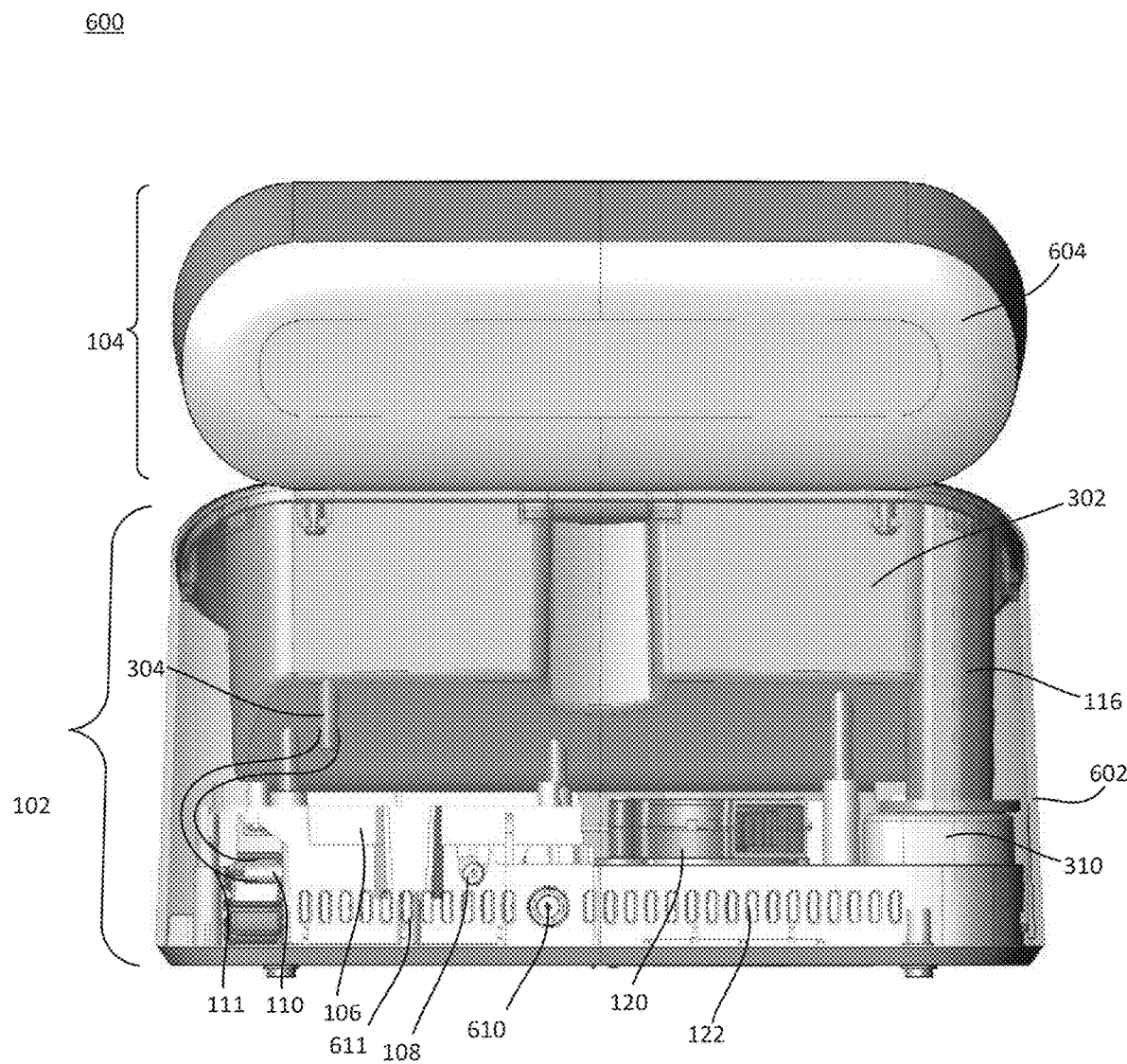
FIG. 6F is a rear view of the disinfection device of FIG. 6F, with certain elements transparent to allow viewing of internal components of the device.

The sanitization chamber 112 includes an open end that is defined at least in part by a rim 612, as best shown in FIGS. 6C and 6E. The lid 104 is configured to form a gas tight seal with rim 612 when lid 104 is in the closed position. In that regard and as best shown in FIG. 6C, lid include a gasket 614 that is configured to form a seal between the lid 104 (or, more particularly, a shoulder of lid 104) and rim 612. For example and as shown in FIG. 6C, lid 104 may be in the form of a lid insert 616 that is configured to be inserted within a cavity defined by lid outer wall 604. Lid insert 616 may define an internal cavity that has a perimeter surface with an outwardly extending flange. When configured in that manner, gasket 614 may be configured to extend around the outwardly extending flange and to facilitate the formation of a gas tight seal between the outwardly extending flange and rim 612.

Sanitization chamber 112 may include one or more supports 618, as best shown in FIGS. 6D and 6E. When used, the supports 618 may be configured to support one or more articles to be sanitized within sanitization chamber 112.

Like the previous embodiments disinfection device 600 includes a sanitization chamber 112 that includes at least one exhaust port 114. In this embodiment the at least one exhaust port 114 is in the form of a plurality of openings through a sidewall of sanitization chamber 112, as best shown in FIG. 6E. The at least one exhaust port 114 is in fluid communication with an exhaust channel 116, as best shown in FIG. 6F. The exhaust channel 116 is fluidly coupled to a filter (not shown) that is disposed within or supported by filter chassis 310. The filter is disposed upstream of and is fluidly coupled to a fan 120, which in this case is a single centrifugal fan. The outlet of fan 120 is fluidly coupled to discharge outlet 122, which in this case is a plurality of openings formed through an outer wall of base 102. An indicator 316 may be provided on the outside of base 102, as best shown in FIG. 6A. In this embodiment the indicator 316 is in the form of a light strip/light pipe that is configured to indicate a status of the disinfection device 600, e.g., whether disinfection device 600 is conducting a sanitizing or termination operation.

Like the other embodiments, disinfection device 600 includes a controller and a user interface (both not shown). The user interface may include one or more buttons or other interactive elements that allow a user to initiate a disinfection operation and/or a termination operation. In embodiments, the lid 104 may form part of the user interface for the disinfection device 600. For example, in embodiments the lid 104 may include a lid sensor that is configured to provide a lid position signal to the controller, wherein the lid position signal is indicative of the position of lid 104. In embodiments the lid sensor may be provided by one or more of lower catch 606a and upper catch 606b, which may be configured as hall sensors. In any case, the controller may determine a position of the lid based at least in part on the lid position signal, as described above. As discussed above, when the lid is in the closed position the controller may permit execution of disinfection operations, and when the lid is in the open position the lid may prevent execution of disinfection operations and may cause the disinfection device 600 to perform one or more termination operations.

During a disinfection operation, the lid 104 of disinfection device 600 is in the closed position (FIGS. 6A and 6B) and only a first flow path is provided through the device. The first flow path extends through sanitizing gas supply 106, sanitization chamber 112, exhaust channel 116, filter 118, and fan 120. A restricted portion of the first flow path is defined at least in part by one or more passageways extending through the sanitizing gas supply 106 and/or an inlet or outlet therefrom. During the disinfection operation the controller causes the fan 120 and sanitizing gas supply 106 to operate. More specifically, the controller causes the ozone generator within sanitizing gas supply 106 to generate ozone, and causes the fan 120 to run in a first flow condition. During the disinfection operation the fan generates a high static pressure within disinfection device 600 and causes gas to flow through the first flow path at a first (relatively low) flow rate. This causes ozone to flow from the sanitizing gas supply 106 into sanitization chamber 112, where it can sanitize an article therein.

While a disinfection operation is conducted the controller monitors disinfection device 600 for the occurrence of a termination condition that would provoke the performance of a termination operation consistent with the present disclosure. Examples of such termination conditions include the opening of lid 104, detection of a threshold amount of ozone gas downstream of the filter 118, detection of leakage of ozone (e.g., from an inlet to sanitizing gas supply 106 or at another location), the running of a disinfection operation for a defined time period (i.e., sanitizing time) combinations thereof, and the like. In particular, the controller monitors the position of lid 104, e.g., via a lid position signal provided by a lid position sensor as described above.

When the controller determines that the lid has been opened (or that another termination condition has occurred) during a disinfection operation or within a threshold time period following a disinfection operation, the controller may cause disinfection device 600 to perform a termination operation consistent with the present disclosure. During a termination operation, the lid 104 is open (or is caused to open by controller 124), a second flow path is provided through disinfection device 600, and the controller causes the fan 120 to operate in a second flow condition. The second flow path extends from a chamber opening to sanitization chamber, through exhaust ports 114, through exhaust channel 116, through filter 118, through fan 120, and through discharge outlet 122. Consistent with the foregoing discussion, the size (cross sectional area) of the passages of the second flow path may be relatively large compared to the size (cross sectional area) of the restricted portion of the first flow path and/or the fan intake. As such, the second flow path is less restricted than the first flow path. Operation of the fan 120 in the second flow condition causes copious amounts of air to be drawn into the chamber opening and through the second flow path. The incoming air dilutes and entrains the sanitizing gas through the exhaust port 114, causing rapid evacuation of the sanitizing gas from the sanitization chamber 112 over an exhaust period as described above.

Figure 7A:
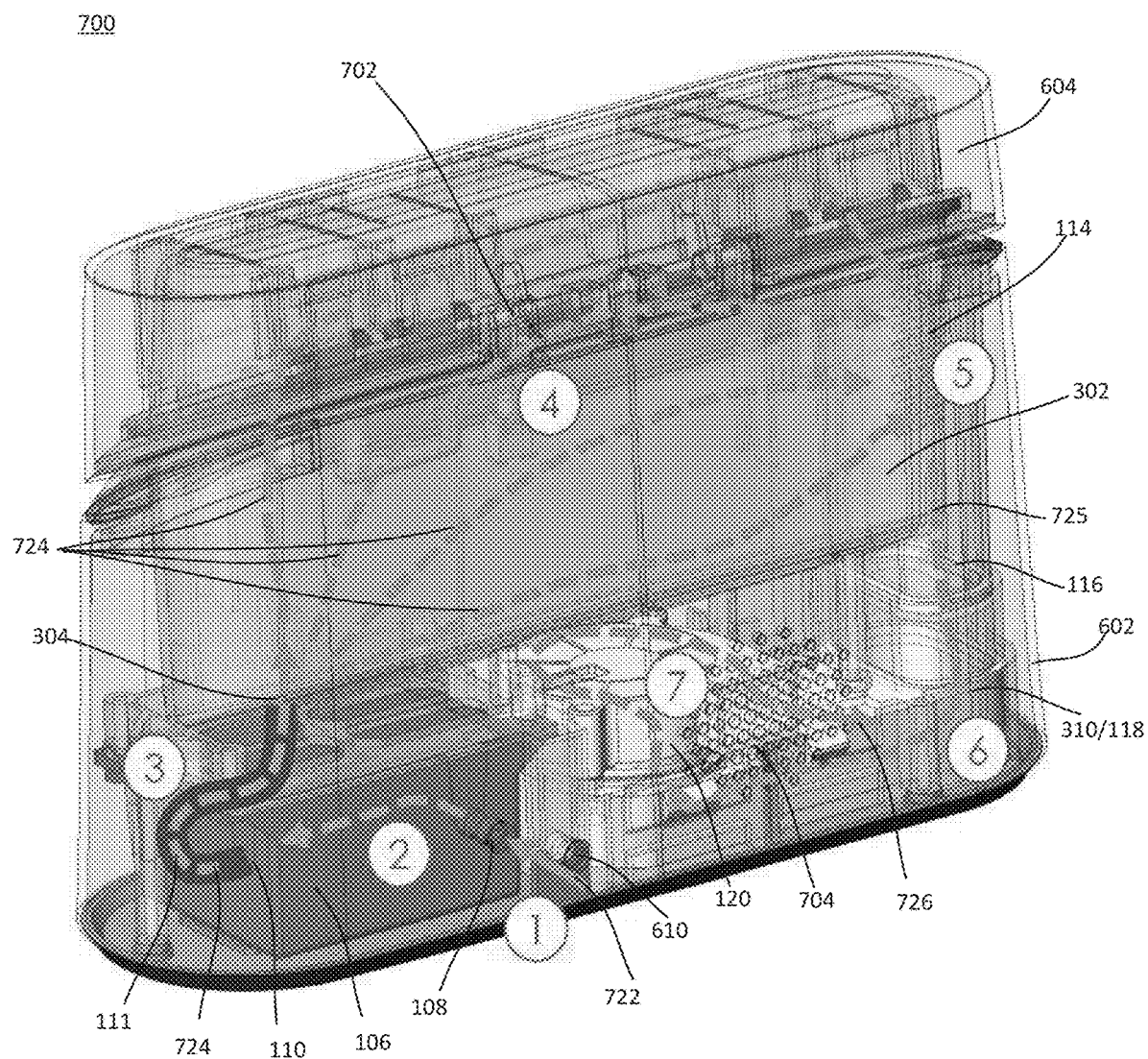
FIG. 7A is a rear perspective view of another example of a disinfection device consistent with the present disclosure, with a closed lid and certain elements transparent to allow viewing of internal components of the device.
Figure 7B:
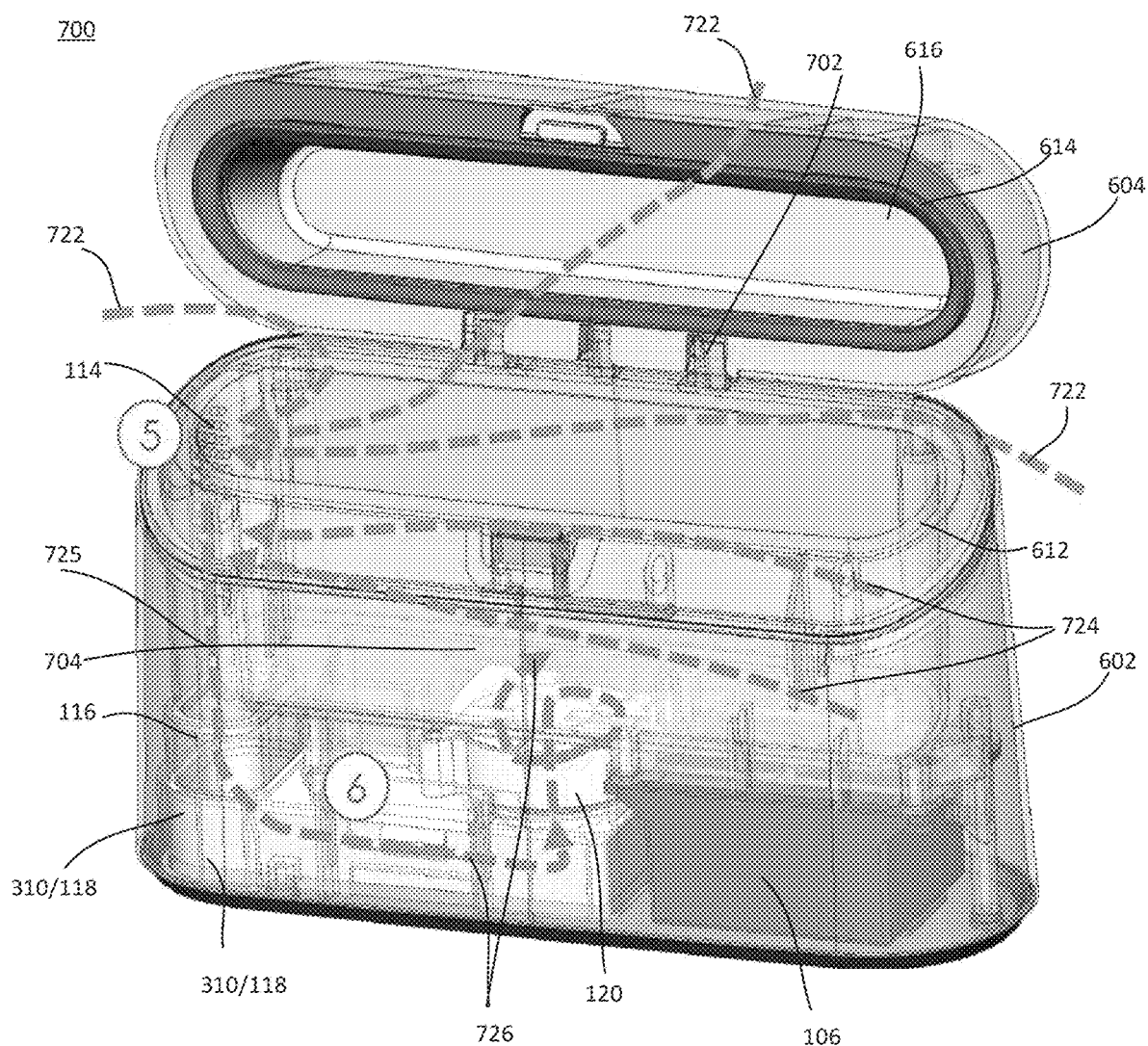
FIG. 7B is a front perspective view of the disinfection device FIG. 7B, with the lid open and certain elements transparent to allow viewing of internal components of the device.

FIGS. 7A and 7B illustrate another example of a disinfection device consistent with the present disclosure, with certain elements transparent. As shown, sanitization system 700 includes many of the same components as disinfection device 600. As the nature and function of such components is the generally the same as the components of disinfection device 600, for brevity such components are not described again in detail. Sanitization system 700 differs from disinfection device 600 in that it includes a hinge 702 that is configured differently than hinge 608, and it includes a discharge outlet 704 that is configured differently than discharge outlet 122. More specifically, hinge 702 is a multipart hinge, and discharge outlet 704 includes a plurality of openings through base outer wall 602.

For clarity and ease of understanding, FIG. 7A illustrates the flow of gas through sanitization system 700 during a disinfection operation, and FIG. 7B illustrates the flow of gas through sanitization system 700 during a termination operation. During a disinfection operation (FIG. 7A) a controller (not shown) causes sanitizing gas supply 106 and fan 120 to run. Because lid 104 is closed fan 120 operates in a first flow condition, and gas is drawn through a first flow path in the sanitization system 700. More specifically air 722 is drawn into sanitizing gas supply 106 via inlet 108, as generally shown at 1. At least a portion of the air 722 flows through the sanitizing gas supply 106 as generally shown at 2. The sanitizing gas supply converts at least a portion of the air 722 into a sanitizing gas 724 (e.g., ozone) in any suitable manner. The sanitizing gas 724 is drawn by the fan 120 through distribution line 111 (as generally shown at 3) and into sanitization chamber 112 (as generally shown at 4). At least a portion of the sanitizing gas 724 within the sanitization chamber 112 is drawn through the exhaust port 114 and into exhaust channel 116 (as generally shown at 5) to form an unfiltered exhaust stream 725. The unfiltered exhaust stream 725 flows through the exhaust channel 116 and through a filter 118 disposed within a filter chassis 310 (as generally shown at 6) to form a filtered exhaust stream 726. The filtered exhaust stream 726 passes through fan 120 as generally shown at 7 and is exhausted through discharge outlet 704.

During a termination operation (FIG. 7B) the controller stops or prevents the operation of sanitizing gas supply 106, and causes fan 120 to run for at least an exhaust period. Because lid 104 is open fan 120 operates in a second flow condition and gas is drawn through the first flow path and a second flow path through the sanitization system 700. More specifically, copious amounts of external air 722 is drawn into a chamber opening that is exposed by lid 104 and into sanitization chamber 112. The incoming air dilutes and entrains sanitizing gas 724 that may be present in the sanitization chamber 112. The resulting mixture flows through exhaust port 114 thereby exhausting all or substantially all of the sanitizing gas from the sanitization chamber within an exhaust period. Gas flowing through the exhaust port 114 is conveyed into the exhaust channel 116 as an unfiltered exhaust stream 725, as generally shown at 5. The unfiltered exhaust stream 725 is conveyed through a filter 118 disposed within a filter chassis 310 (as generally shown at 6) to form a filtered exhaust stream 726. The filtered exhaust stream 726 passes through fan 120 as generally shown and is exhausted through discharge outlet 704.

Figure 8:
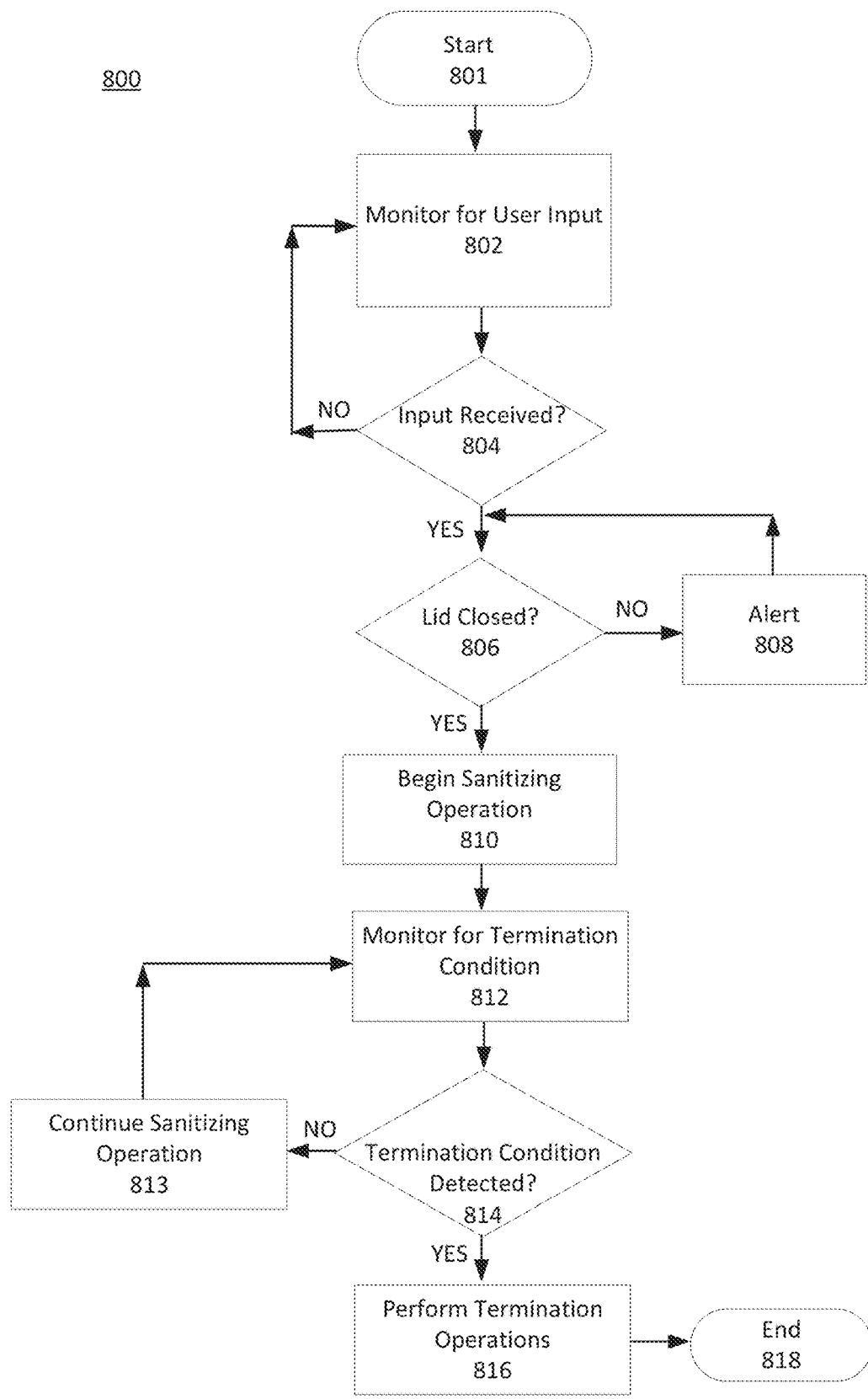
FIG. 8 is a flow diagram of example operations of one example of a method of disinfecting articles consistent with the present disclosure.

FIG. 8 is a flow diagram of example operations of a method of sanitizing articles consistent with the present disclosure. As shown, method 800 begins at block 801. The method may then proceed to block 802, during which a controller of a sanitization system may monitor for a user input (e.g., via a user interface) that initiates a disinfection operation. The method then proceeds to block 804, pursuant to which a decision is made as to whether such a user input has been received. If not, the method loops back to block 802, but if so the method proceeds to block 806. Pursuant to block 806, the controller may determine whether a lid of the sanitization system is in a closed position. The controller may perform that function in any suitable manner, such as by determining the position of the lid at least in part from one or more lid positions signals from a lid position sensor. If the lid is not closed the method may proceed to block 808, pursuant to which an alert may be provided. The alert may be an audio, visual, or audiovisual indicator that notifies a user that the lid is open. The method may then loop back to block 806.

When it is determined pursuant to block 806 that the lid is closed the method may proceed to block 810, pursuant to which a disinfection operation may be performed. The disinfection operation may include causing a sanitizing gas supply to operate and causing a fan to run in a first flow condition, as previously described. The method may then proceed to block 812, pursuant to which the controller may monitor for the occurrence of a termination condition, such as but not limited to the termination conditions described above. If a termination condition is not detected the method may proceed to block 813, pursuant to which the disinfection operation continues. From there, the method may loop back to block 812.

When a termination condition (e.g., opening of the lid, expiration of a sanitization period, etc.) is detected, the method proceeds from block 814 to block 816, pursuant to which one or more termination operations is conducted. As described above, such operations may include discontinuing/preventing operation of the sanitizing gas supply and causing the fan to run in the second flow condition so as to exhaust all or substantially all of the sanitizing gas from the sanitization chamber. The method may then proceed to block 818 and end.

EXAMPLES

The following examples are additional non-limiting embodiments of the present disclosure.

Example 1: According to this example there is provided a disinfection device including: a base; a sanitizing gas supply within the base, the sanitizing gas supply configured to supply a sanitizing gas; a sanitization chamber within the base and configured to receive an article at least partially therein, the sanitization chamber including a chamber opening and an exhaust port; a fan within the base, the fan fluidly coupled the exhaust port; and a lid coupled to the base, the lid configured to move between an closed position in which the chamber opening is closed and an open position in which the chamber opening is open; wherein: when the lid is in the closed position the fan is configured to operate in a first flow condition; when the lid is in the open position the fan is configured to operate in a second flow condition; the first flow condition is a low flow, high static pressure condition; and the second flow condition is a high flow, low static pressure condition.

Example 2: This example includes any or all of the features of example 1, wherein when the lid is in the closed position, only a first flow path is defined through the disinfection device, the first flow path including a restricted portion.

Example 3: This example includes any or all of the features of example 2, wherein the first flow path extends through the sanitizing gas supply, the sanitization chamber, the exhaust port, and the fan.

Example 4: This example includes any or all of the features of example 3, further including a filter, wherein the first flow path extends through the sanitizing gas supply, the sanitization chamber, the exhaust port, the filter and the fan.

Example 5: This example includes any or all of the features of example 2, wherein the restricted portion is at least partially defined by at least one passage in the sanitizing gas supply.

Example 6: This example includes any or all of the features of example 5, wherein the sanitizing gas supply includes an inlet and an outlet, and the restricted portion is at least partially defined by the inlet, the outlet, or both the inlet and the outlet.

Example 7: This example includes any or all of the features of example 5, wherein the fan includes a fan intake, the restricted portion includes a passageway that has a first cross sectional area, the fan intake has a second cross sectional area, and the first cross sectional area is less than the second cross sectional area.

Example 8: This example includes any or all of the features of any one of examples 1 to 7, wherein in the first flow condition the fan is configured to cause gas to flow at a first flow rate that ranges from greater than 0 to about 1 liters per minute (LPM).

Example 9: This example includes any or all of the features of any one of examples 1 to 8, wherein in the second flow condition the fan is configured to cause gas to flow at a second flow rate that is greater than or equal to about 100 liters per minute (LPM).

Example 10: This example includes any or all of the features of example 1, wherein: in the first flow condition the fan is configured to cause gas to flow at a first rate that is less than or equal to about 0.5 liters per minute (LPM); and in the second flow condition the fan is configured to cause gas to flow at a second rate that is greater than 100 LPM.

Example 11: This example includes any or all of the features of any one of examples 1 to 10, wherein in the second flow condition, the fan is configured to exhaust all or substantially all sanitizing gas from the sanitization chamber within an exhaust period, wherein the exhaust period is less than or equal to about 5 seconds.

Example 12: This example includes any or all of the features of example 11, wherein the exhaust period is less than or equal to about 1 second.

Example 13: This example includes any or all of the features of example 11, wherein the exhaust period is less than or equal to about 0.5 seconds.

Example 14: This example includes any or all of the features of any one of examples 1 to 13, wherein the sanitizing gas supply includes an ozone generator.

Example 15: This example includes any or all of the features of any one of examples 1 to 14, wherein the fan is a centrifugal fan, an axial fan, or a combination thereof.

Example 16: This example includes any or all of the features of example 15, wherein the fan is a centrifugal fan.

Example 17: According to this example there is provided a method of sanitizing an article with a disinfection device including a base, a lid, a sanitizing gas supply within the base, a sanitization chamber within the base, a fan within the base, and a controller the sanitization chamber including an exhaust port and a chamber opening, the method including: determining, with the controller, whether the lid in a closed position; when the lid is in the closed position, initiating operation of a sanitizing gas supply and a fan in a first flow condition with the controller; monitoring, with the controller, for a termination condition; and in response to detection of a termination condition, disabling operation of the sanitizing gas supply with the controller and causing the fan to operate in a second flow condition with the controller; wherein: the first flow condition is a low flow, high static pressure condition; and the second flow condition is a high flow, low static pressure condition.

Example 18: This example includes any or all of the features of example 17, wherein when the lid is in the closed position, only a first flow path is defined through the disinfection device, the first flow path including a restricted portion.

Example 19: This example includes any or all of the features of example 18, wherein the first flow path extends through the sanitizing gas supply, the sanitization chamber, the exhaust port, and the fan.

Example 20: This example includes any or all of the features of example 19, wherein the disinfection device further includes a filter, and the first flow path extends through the sanitizing gas supply, the sanitization chamber, the exhaust port, the filter and the fan.

Example 21: This example includes any or all of the features of example 18, wherein the restricted portion is at least partially defined by at least one passage in the sanitizing gas supply.

Example 22: This example includes any or all of the features of example 21, wherein the sanitizing gas supply includes an inlet and an outlet, and the restricted portion is at least partially defined by the inlet, the outlet, or both the inlet and the outlet.

Example 23: This example includes any or all of the features of example 21, wherein the fan includes a fan intake, the restricted portion includes a passageway that has a first cross sectional area, the fan intake has a second cross sectional area, and the first cross sectional area is less than the second cross sectional area.

Example 24: This example includes any or all of the features of any one of examples 17 to 23, wherein in the first flow condition the fan causes gas to flow at a first flow rate that ranges from greater than 0 to about 1 liters per minute (LPM).

Example 25: This example includes any or all of the features of any one of examples 17 to 24, wherein in the second flow condition the fan causes gas to flow at a second flow rate that is greater than or equal to about 100 liters per minute (LPM).

Example 26: This example includes any or all of the features of example 18, wherein: in the first flow condition the fan causes gas to flow at a first rate that is less than or equal to about 0.5 liters per minute (LPM); and in the second flow condition the fan causes gas to flow at a second rate that is greater than 100 LPM.

Example 27: This example includes any or all of the features of any one of examples 17 to 26, wherein in the second flow condition the fan causes all or substantially all sanitizing gas in the sanitization chamber to exhaust through the exhaust port within an exhaust period, wherein the exhaust period is less than or equal to about 5 seconds.

Example 28: This example includes any or all of the features of example 27, wherein the exhaust period is less than or equal to about 1 second.

Example 29: This example includes any or all of the features of example 27, wherein the exhaust period is less than or equal to about 0.5 seconds.

Example 30: This example includes any or all of the features of any one of examples 17 to 29, wherein the sanitizing gas supply includes an ozone generator.

Example 31: This example includes any or all of the features of any one of examples 17 to 30, wherein the fan is a centrifugal fan, an axial fan, or a combination thereof.

Example 32: This example includes any or all of the features of example 31, wherein the fan is a centrifugal fan.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the claims.

What is claimed is:

1. A disinfection device comprising:
   a base;
   a sanitizing gas supply within the base, the sanitizing gas supply configured to supply a sanitizing gas;
   a sanitization chamber within the base and configured to receive an article at least partially therein, the sanitization chamber comprising a chamber opening and an exhaust port;
   a fan within the base, the fan fluidly coupled the exhaust port; and
   a lid coupled to the base, the lid configured to move between a closed position in which the chamber opening is closed and an open position in which the chamber opening is open; wherein:
   when the lid is in the closed position the fan is configured to operate in a first flow condition;
   when the lid is in the open position the fan is configured to operate in a second flow condition;
   the first flow condition is a low flow, high static pressure condition; and
   the second flow condition is a high flow, low static pressure condition.

2. The disinfection device of claim 1, wherein when the lid is in the closed position, only a first flow path is defined through the disinfection device, the first flow path comprising a restricted portion.

3. The disinfection device of claim 2, wherein the first flow path extends through the sanitizing gas supply, the sanitization chamber, the exhaust port, and the fan.

4. The disinfection device of claim 3, further comprising a filter, wherein the first flow path extends through the sanitizing gas supply, the sanitization chamber, the exhaust port, the filter and the fan.

5. The disinfection device of claim 2, wherein the restricted portion is at least partially defined by at least one passage in the sanitizing gas supply.

6. The disinfection device of claim 5, wherein the sanitizing gas supply comprises an inlet and an outlet, and the restricted portion is at least partially defined by the inlet, the outlet, or both the inlet and the outlet.

7. The disinfection device of claim 5, wherein the fan comprises a fan intake, the restricted portion includes a passageway that has a first cross sectional area, the fan intake has a second cross sectional area, and the first cross sectional area is less than the second cross sectional area.

8. The disinfection device of claim 1, wherein:
   in the first flow condition the fan is configured to cause gas to flow at a first rate that is less than or equal to about 0.5 liters per minute (LPM); and
   in the second flow condition the fan is configured to cause gas to flow at a second rate that is greater than 100 LPM.

9. The disinfection device of claim 1, wherein in the second flow condition, the fan is configured to exhaust all or substantially all sanitizing gas from the sanitization chamber within an exhaust period, wherein the exhaust period is less than or equal to about 5 seconds.

10. The disinfection device of claim 9, wherein the exhaust period is less than or equal to about 1 second.

11. The disinfection device of claim 1, wherein the sanitizing gas supply comprises an ozone generator.

12. The disinfection device of claim 1, wherein the fan is a centrifugal fan, an axial fan, or a combination thereof.

13. A method of sanitizing an article with a disinfection device comprising a base, a lid, a sanitizing gas supply within the base, a sanitization chamber within the base, a fan within the base, and a controller the sanitization chamber comprising an exhaust port and a chamber opening, the method comprising:
    determining, with the controller, whether the lid in a closed position;
    when the lid is in the closed position, initiating operation of a sanitizing gas supply and a fan in a first flow condition with the controller;
    monitoring, with the controller, for a termination condition; and
    in response to detection of a termination condition, disabling operation of the sanitizing gas supply with the controller and causing the fan to operate in a second flow condition with the controller; wherein:
    the first flow condition is a low flow, high static pressure condition; and
    the second flow condition is a high flow, low static pressure condition.

14. The method of claim 13, wherein when the lid is in the closed position, only a first flow path is defined through the disinfection device, the first flow path comprising a restricted portion.

15. The method of claim 14, wherein the first flow path extends through the sanitizing gas supply, the sanitization chamber, the exhaust port, and the fan.

16. The method of claim 15, wherein the disinfection device further comprises a filter, and the first flow path extends through the sanitizing gas supply, the sanitization chamber, the exhaust port, the filter and the fan.

17. The method of claim 14, wherein the restricted portion is at least partially defined by at least one passage in the sanitizing gas supply.

18. The method of claim 17, wherein the sanitizing gas supply comprises an inlet and an outlet, and the restricted portion is at least partially defined by the inlet, the outlet, or both the inlet and the outlet.

19. The method of any one of claim 13, wherein in the second flow condition the fan causes all or substantially all sanitizing gas in the sanitization chamber to exhaust through the exhaust port within an exhaust period, wherein the exhaust period is less than or equal to about 5 seconds.

20. The method of claim 13, wherein the sanitizing gas supply comprises an ozone generator.

* * * * *